US006956147B2

(12) United States Patent
Chye et al.

(10) Patent No.: US 6,956,147 B2
(45) Date of Patent: Oct. 18, 2005

(54) GENETICALLY MODIFIED PLANTS WITH ENHANCED RESISTANCE TO FUNGAL DISEASES AND A METHOD OF PRODUCTION THEREOF

(75) Inventors: Mee Len Chye, Hong Kong (CN); Kai-Jun Zhao, Beijing (CN)

(73) Assignee: The University of Hong Kong, Hong Kong (CN)

( * ) Notice: Subject to any disclaimer, the term of this patent is extended or adjusted under 35 U.S.C. 154(b) by 202 days.

(21) Appl. No.: 10/300,819

(22) Filed: Nov. 20, 2002

(65) Prior Publication Data

US 2003/0097682 A1 May 22, 2003

Related U.S. Application Data

(60) Provisional application No. 60/331,749, filed on Nov. 20, 2001.

(51) Int. Cl.$^7$ .................. C12N 15/09; C12N 15/29; C12N 15/82; A10H 5/00
(52) U.S. Cl. .................. 800/279; 800/278; 800/320; 800/317; 800/298; 800/295; 435/419; 435/468; 435/320.1
(58) Field of Search .................. 800/279, 278, 800/320, 317, 298, 295, 317.2, 306; 435/419, 320.1, 468, 69.1; 536/23.2, 23.6, 24.1

(56) References Cited

U.S. PATENT DOCUMENTS 5,670,706 A * 9/1997 Cornelissen et al. ........ 800/205
5,994,625 A * 11/1999 Melchers .................... 800/279

OTHER PUBLICATIONS

Abeles and Forrence, 1970, "Temporal and hormonal control of β–1,3–glucanase in *Phaseolus vulgaris* L." Plant Physiol. 45:395–400.
Beintema, 1994, "Structural features of plant chitinases and chitin–binding proteins", FEBS Lett. 350:159–163.
Berglund et al., 1995, "A proline–rich chitinase from *Beta vulgaris*", Plant Mol. Biol. 27:211–216.
Boller et al., 1983, "Chitinase in bean leaves: induction by ethylene, purification, properties, and possible function", Planta 157:22–31.
Boller, 1985, "Induction of hydrolases as a defense reaction against pathogens", In: *Cellular and Molecular Biology of Plant Stress*, J.L. Key and T. Kosuge (eds), Alan R. Liss, New York, pp 247–262.
Boller, 1992, "Biochemical analysis of chitinases and β–1, 3–glucanases", In: *Molecular Plant Pathology vol. II, A Practical Approach*, S. J. Gurr, M.J. Mcpherson and D. J. Bowles (eds), IRL press, Oxford. pp. 23–30.
Bradford, 1976, "A rapid and sensitive method for the quantification of microgram quanities of protein utilizing the principle of protein–dye binding", Anal. Biochem 72: 248–254.

Broglie et al., 1991, "Transgenic plants with enhanced resistance to the fungal pathogen *Rhizoctonia solani*", Science 254 1194–1197.
Broglie et al., 1986, "Ethylene–regulated gene expression: molecular cloning of the genes encoding an endochitinase from *Phaseolus vulgaris*", Proc. Natl. Acad. Sci. USA 83:6820–6824.
Broglie et al., 1984, "Light–regulated expression of a pea ribulose–1,5–biphosphate carboxylase small subunit gene in transformed plant cells", Science 224:838–843.
Chrispeels and Raikhel, 1991, "Lectins, lectin genes, and their role in plant defense", Plant Cell 3:1–9.
Chye and Cheung, 1995, "β–1,3–glucanase is highly–expressed in laticifers of *Hevea brasiliensis*", Plant Mol. Biol. 29:397–402.
Dietze et al., 1995, "*Agrobacterium*–mediated transformation of potato (*Solanum tuberosum*)", In: *Gene Transfer to Plants*, Potrykus and Spangenberg (eds),, Cold Spring Harbor Laboratory, New York, pp. 24–29.
Does et al., 1999, "Processing, targeting and antifungal activity of stinging nettle agglutinin in transgenic tobacco", Plant Physiol. 120:421–431.
Fung, et al., 2002, "Tobacco–expressed *Brassica juncea* chitinase BjCHI1 shows antifungal activity in vitro", Plant Mol. Biol. 50:283–294.
Hamel and Bellemare, 1993, "Nucleotide sequence of a *Brassica napus* endochitinase gene". Plant Physiol. 101:1403.
Iseli et al., 1993, "The N–terminal cysteine–rich domain of tobacco class 1 chitinase is essential for chitin binding but not for catalytic or antifungal activity", Plant Physiol. 103:221–226.
Jach et al., 1995, "Enhanced quantitative resistance against fungal disease by combinatorial expression of different barley antifungal proteins in transgenic tobacco", Plant J. 8:97–109.
Kush et al., 1990, "Laticifer–specific gene expression in *Hevea brasiliensis* (rubber tree)", Proc. Natl. Acad. Sci. USA 87:1787–1790.
Lasserre et al., 1996, "Structure and expression of three genes encoding ACC oxidase homologs from melon (*Cucumis melo* L.)", Mol. Gen. Genet. 251:81–90.
Lerner and Raikhel, 1992, "The gene for stinging nettle lectin (*Urtica dioica* agglutinin) encodes both a lectin and a chitinase", J. Biol. Chem. 267:11085–11091.

(Continued)

Primary Examiner—Medina A. Ibrahim
(74) Attorney, Agent, or Firm—Dickstein, Shapiro, Morin & Oshinsky, LLP.

(57) ABSTRACT

The present invention discloses genetically modified plants, such as potato plants. The plants are more resistant to a pathogen of interest following transformation of plant cells with a chimeric gene comprising a chitinase gene and β-1,3-glucanase gene. The invention also provides a method of enhancing the resistance of plants to pathogens by introducing a Brassica chitinase gene encoding two or more chitin-binding domains and β-1,3-glucanase gene and expressing the chitinase gene and β-1,3-glucanase gene.

26 Claims, 16 Drawing Sheets

OTHER PUBLICATIONS

Figures 1A, 1B:
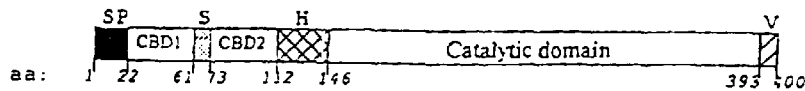

Levorson and Chlan, 1997, "Plant chitinase consensus sequences", Plant Mol. Biol. Reptr. 15:122–133.

Lin et al., 1995, "Genetic engineering of rice for resistance to sheath blight", Bio/Technology 13:686–691.

Margis–Pinheiro et al., 1991, "Isolation of a complementary DNA encoding the bean PR4 chitinase: an acidic enzyme with an amino–terminus cysteine–rich domain", Plant Mol. Biol. 17:243–253.

Mauch et al., 1988, "Antifungal hydrolases in pea tissue II. Inhibition of fungal growth by combinations of chitinase and β–1,3–glucanase", Plant Physiol. 88:936–942.

Nagy et al., 1988, "Analysis of gene expression in transgenic plants", In: *Plant Molecular Biology Manual*, Gelvin and Cshilperoort (eds), Kluwer Academic Publishers, Dordrecht, pp. B4:11–13.

Payne et al., 1990, "Isolation of complementary DNA clones encoding pathogenesis–related proteins P and Q, two acidic chitinases from tobacco", Proc. Natl. Acad. Sci. USA 87:98–102.

Peumans and Van Damme, 1995, "Lectins as plant defense proteins", Plant Physiol. 109:347–352.

Pua et al., 1992, "Isolation and sequence analysis of a cDNA clone encoding ethylene–forming enzyme in *Brassica juncea*. (L.) Czern & Coss", Plant Mol. Biol. 19:541–544.

Rasmussen et al., 1992, "Cloning and characterization of a pathogen–induced chitinase in *Brassica napus*", Plant Mol. Biol. 20:277–287.

Samac et al., 1990, "Isolation and characterization of the genes encoding basic and acidic chitinase in *Arabidopsis thaliana*", Plant Physiol. 93:907–914.

Schlumbaum et al., 1986, "Plant chtinases are potent inhibitors of fungal growth", Nature 324:365–367.

Shinshi et al., 1990, "Structure of a tobacco endochitinase gene: evidence that different chitinase genes can arise by transportation of sequences encoding a cysteine–rich domain", Plant Mol. Biol. 14:357–368.

Van Parijs et al., 1991, "Hevein: an atifungal protein from rubber–tree (*Hevea brasiliensis*) latex", Planta 183:258–264.

Verburg et al., 1992, "Identification of an essential tyrosine residue in the catalytic site of a chitinase isolated from *Zea mays* that is selectively modified during inactivation with 1–ethyl–3–(3–dimethylaminopropyl)–carbodiimide", J. Biol. Chem. 267:3886–3893.

Verburg and Huynh, 1991, "Purification and Characterization of an antifungal chitinase from *Arabidopsis thaliana*", Plant Physiol. 95:450–455.

Ward et al., 1989, "Binding activities of a repertoire of single immunoglobulin variable domains secreted from *Escherichia coli*" Nature 341:544–546.

Wirth and Wolf. 1990, "Dye–labelled substrates for the assay and detection of chitinase and lysozyme activity", J. Microbiol. Meth. 12:197–205.

Yanisch–Perron et al., 1985, "Improved M13 phage cloning vectors and host strains: nucleotide sequences of the M13mp18 and pUC19 vectors", Gene 33:103–119.

Zhao and Chye, 1999, "Methyl jasmonate induces expression of a novel *Brassica juncea* chitinase with two chitin–binding domains", Plant Mol. Biol. 40:1009–1018.

Zhu et al., 1994, "Enhanced protection against fungal attack by constitutive co–expression of chitinase and glucanase genes in transgenic tobacco", Bio/Technology 12:807–812.

Benhamou et al., Antifungal effect of bean endochitinase on Rhizoctonia solani: ultrastructural changes and cytochemical aspects of chitin breakdown. Can J Microbiol. Mar. 1993;39(3):318–28.

* cited by examiner

FIG. 2A

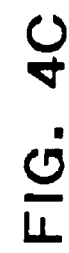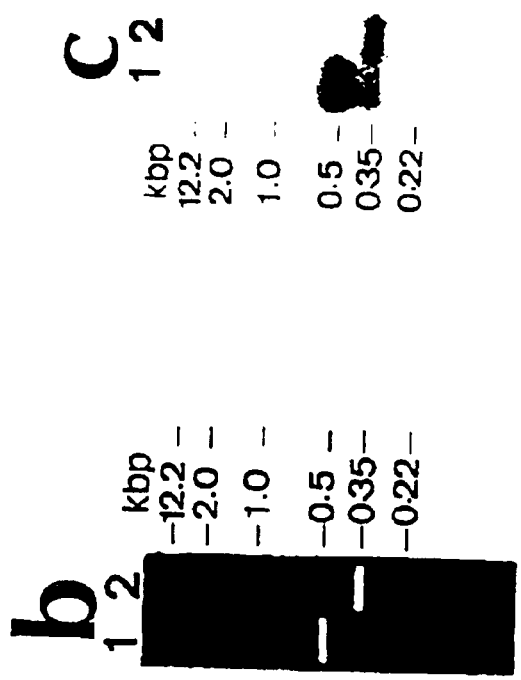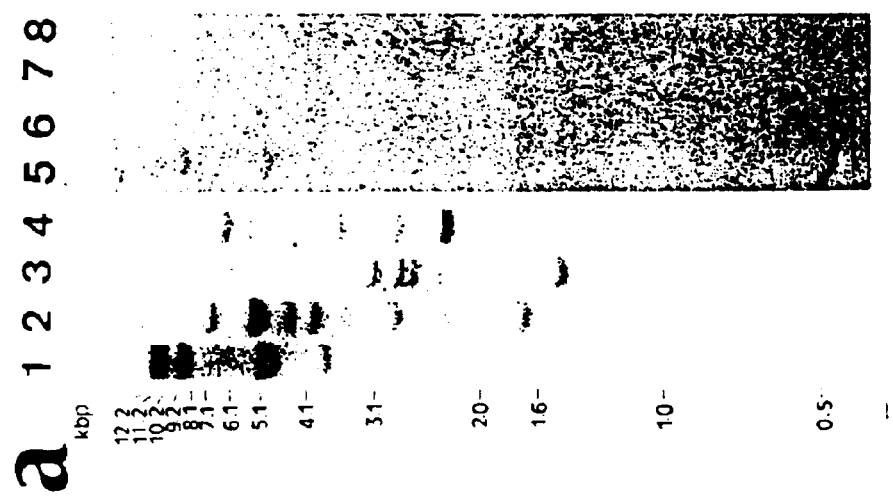
FIG. 4C
FIG. 4B
FIG. 4A

```
AAATTATAAG CAACTTTCTT CTAATTTCCC CCCTTCTTAA TGGCTATCTC CTCTTCAACT
TCAGGAACTA GTAGTTCCTT CCCCTCAAGA ACTACTGTCA TGCTTCTTCT GTTTTTCTTT
GCAGCAAGCG TTGGTATAAC AGATGCCCAG GTAGGTGTTT GCTATGGAAT GCAAGGCAAC
AACCTTCCAC CTGTTTCAGA GGTCATAGCT CTCTATAAAA AATCTAACAT CACGAGAATG
AGAATTTATG ATCCAAATCG AGCAGTATTG GAAGCCCTTA GAGGCTCAAA CATTGAACTC
ATACTAGGTG TTCCAAACTC AGATCTCCAA AGCCTTACCA ATCCTTCCAA TGCAAAATCA
TGGGTACAAA AAAATGTTCG TGGCTTCTGG TCAAGTGTCC TGTTCAGATA TATAGCAGTT
GGCAACGAAA TTAGTCCTGT CAATAGAGGC ACAGCTTGGT TGGCTCAATT TGTTTTGCCT
GCCATGAGAA ATATACATGA TGCTATAAGA TCAGCTGGTC TTCAAGATCA AATCAAGGTC
TCCACTGCAA TTGACTTGAC CCTGGTAGGA AATTCCTACC CTCCTTCTGC AGGTGCTTTC
AGGGATGATG TTAGATCATA CTTGGACCCA ATTATTGGAT TTCTATCCTC TATCAGGTCA
CCTTTACTTG CCAATATTTA TCCTTACTTT ACTTATGCTT ATAATCCAAG GGATATTTCC
CTTCCCTATG CTTTGTTCAC TTCACCATCA GTTGTTGTGT GGGATGGTCA GCGAGGTTAT
AAGAACCTTT TTGATGCAAC GTTGGATGCA TTGTACTCTG CTCTTGAGAG GGCTAGTGGT
GGTTCTCTGG AGGTGGTTGT TTCGGAAAGT GGCTGGCCGT CTGCCGGAGC ATTTGCTGCC
ACATTTGACA ATGGGCGTAC TTATCTCTCA AATTTGATCC AACATGTTAA AGGAGGTACT
CCTAAGAGGC CTAACAGAGC TATAGAGACT TACTTATTTG CCATGTTTGA TGAAAATAAG
AAGCAACCAG AGGTTGAGAA ACACTTTGGA CTTTTCTTTC CTGATAAACG GCCAAAATAT
AATCTCAATT TTGGTGCAGA AAAGAACTGG GATATTTCTA CTGAACACAA TGCAACAATA
CTTTTCCTTA AGAGTGATAT GTGAGATTGT GAGAATTTAA GTACTATATA TATTTCCAAT
GTATGCATGT ATCCATGTAT TAAATAAGAG AACCTTTTCT CA
```

FIG. 5A

```
MAISSSTSGT SSSFPSRTTV MLLLFFFAAS VGITDAQVGV CYGMQGNNLP PVSEVIALYK
KSNITRMRIY DPNRAVLEAL RGSNIELILG VPNSDLQSLT NPSNAKSWVQ KNVRGFWSSV
LFRYIAVGNE ISPVNRGTAW LAQFVLPAMR NIHDAIRSAG LQDQIKVSTA IDLTLVGNSY
PPSAGAFRDD VRSYLDPIIG FLSSIRSPLL ANIYPYFTYA YNPRDISLPY ALFTSPSVVV
WDGQRGYKNL FDATLDALYS ALERASGGSL EVVVSESGWP SAGAFAATFD NGRTYLSNLI
QHVKGGTPKR PNRAIETYLF AMFDENKKQP EVEKHFGLFF PDKRPKYNLN FGAEKNWDIS
TEHNATILFL KSDM
```

FIG. 5B

```
Hb   MAISSSTSGTS-SSFPSRTTVMLLLFFFAASVGITDAQ--VGVCYGMQGN
Np   MD..HKHIALQMAAII..GLLVS.TE.VG..S-.......L..
CII  M.LCIK-NG.L--AAALV.VGLLIC.IQMIG..S-I.....KHA.
CIII        MAHLIV.LL..SVLTL.TLDF.G...--A.....R...
CIV  MALWYLFNKR.LGA--A.LI.VGLLMCNIQM.G..SNI.....KIA.
                                                    97
Hb   NLPPVSEVIALYKKSNITRMRIYDPNRAVLEALRGSNIELILGVPNSDLQ
Np   ....A.Q.VQ...SK..R...L....Q.A.Q........VM........
CII  ...SDQD..N..NANG.RK....N.DTN.FN........I..D..LQ...
CIII G..SPAD.VS.CNRN..R......DQPT.........M.....P..E
CIV  ...SEQD..N...ANG.RK....NSDTNIFKS.N.....I..D...Q..E
                                                    146
Hb   SL-TNPSNAKSWVQKNVRGFWSSVLFRYIAVGNEISPVNRGTAWLAQFVL
Np   NIAA.....NN...R...N..PA.K.........V...T-...SS.TRYL.
CII  ..-.D..R.NG...D.IINHFPD.K.K.......V..G.N.Q--Y.P..A
CIII NVAASQA..DT...N...NY-GN.K.........V..L.ENSKYVP-VL.
CIV  A.-A.S.I.NG...D.I.SHFPY.K.K..SI...V..S.N.Q--YS..L.
                                                    196
Hb   PAMRNIHDAIRSAGLQDQIKVSTAIDLTLVGNSYPPSAGAFRDDVRSYLD
Np   ......RN..S.....NN....SSV.M..I...F...Q.S..N....FI.
CII  ...Q.VYN.LAA..........TYSGILA.T...KDSI..GEFN.FIN
CIII N.....QT..SG...GN........ETG.TTDTS...N.R.K....QFIE
CIV  H..E.VYN.LAA.....K...T..TYSG.LA.T...KDSI..EEFK.FIN
                                                    246
Hb   PIIGFLSSIRSPLLANIYPYFTYAYNPRDISLPYALFTSPSVVVWDGQRG
Np   .....VRR.N....V......S..G............A.N...Q..SL.
CII  ...Q..VQHNL.....V....GHIF.TA.VP.S.....QQE----ANPA.
CIII ...N..VTN.A...V.L....AI.N.A-..K.E......SE...N.NG..
CIV  ...E..ARNNL.........GHI..TV.VP.S....NQQG----TNST.
                                                    295
Hb   YKNLFDATLDALYSALERASGGSLEVVVSESGWPSAGAFAAT-FDNGRTY
Np   .R.....MS..V.A..S..G...I.I..............-TN.AA..
CII  .Q.....L..SM.F.V.K.G.QNV.II........E.NS..T-IE.AQ..
CIII .R.....I...T.....K...S...I............GQL.SI..A...
CIV  .Q.....L..SI.F.V.K.G.PNV.II........E.NS...-IE.AQ..
                                                    342
Hb   LSNLIQHVK--GGTPKRPNRAIETYLFAMFDENKKQPEV-EKHFGLFFPD
Np   YK........--R.S.R...KV............N.N..L-.......S.N
CII  YE...N...SGA....K.GK............N.EGDIT.......S..
CIII NN...S...--..S....SGP....V..L...DQ.D..I-.......SAN
CIV  YR..VN...GGA....K.G.IV.........E.NG..T........Y.N
                                                    374
Hb   KRPKYNLNFG-AEKNWDISTEHNATILFLKSDM
Np   .Q...P.S..FSDRY....A.N...AAS.I.E.
CII  Q.A..Q...N
CIII MQ...QIS.N
CIV  RTA..Q...MYS
```

FIG. 5C a 1 2 3 4 5 6 7 8 9 10

←1.3kb BjCHI1

◄ 18S rRNA b kD  1 2 3 4 5 6 7 8 9 10

46 −

30 −

21.5 − c kD  1 2 3 4 5 6 7 8 9 10

45 −

31 −

21.5 −

FIG. 8

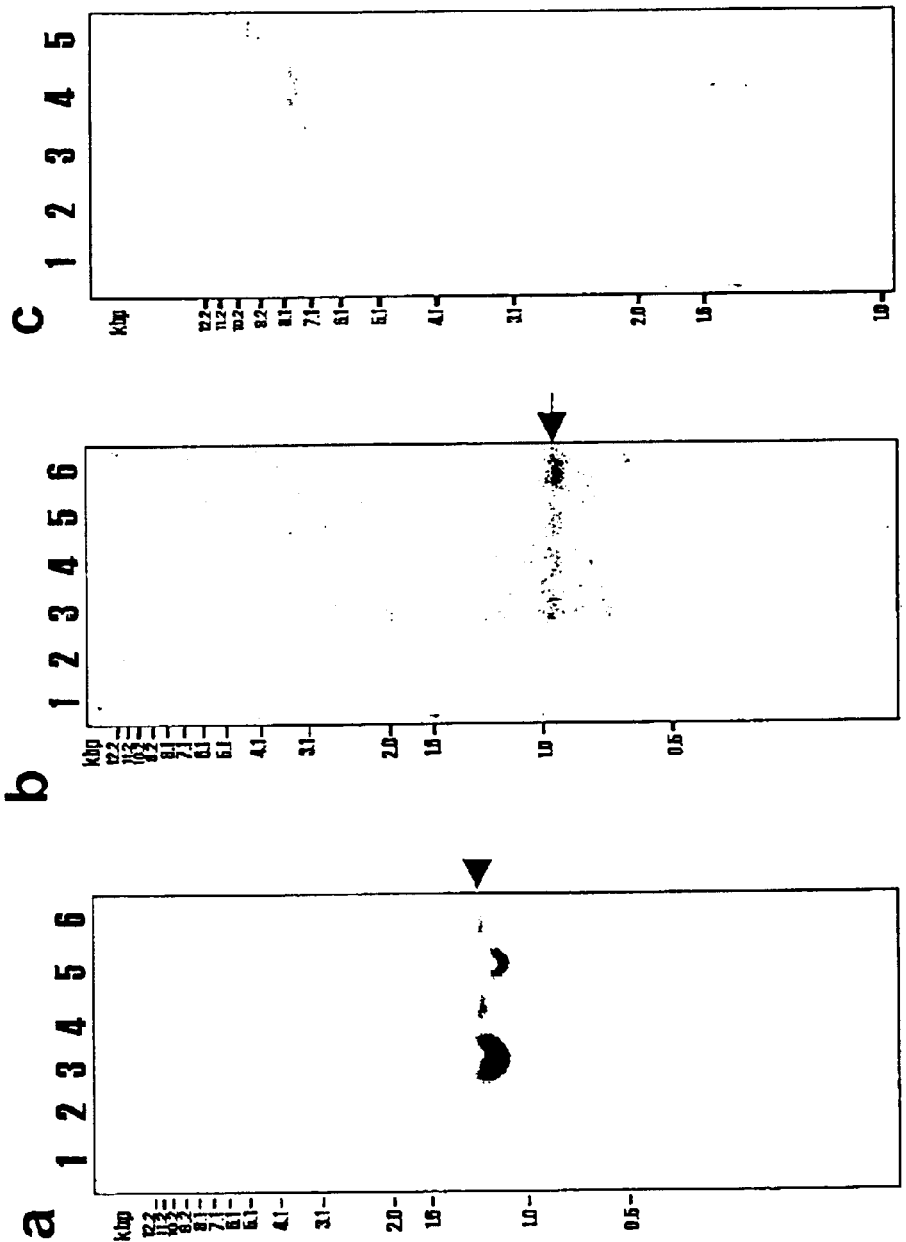

SEQUENCE LISTING

<160> NUMBER OF SEQ ID NOS: 25

<210> SEQ ID NO 1
<211> LENGTH: 1297
<212> TYPE: DNA
<213> ORGANISM: Brassica juncea
<220> FEATURE:
<221> NAME/KEY: CDS
<222> LOCATION: (4)..(1203)

<400> SEQUENCE: 1

```
aac atg aag act tat ctc ctt ctc ctt ctc atc ttc tca ctt ctc tta     48
    Met Lys Thr Tyr Leu Leu Leu Leu Leu Ile Phe Ser Leu Leu Leu
    1               5                   10                  15 tca ttt tcc tcc ggt gag caa tgc ggt agt caa tcc ata ccc gag gga     96
Ser Phe Ser Ser Gly Glu Gln Cys Gly Ser Gln Ser Ile Pro Glu Gly
                20                  25                  30 gca ctc tgc ccc aac ggt cta tgc tgc agc gag gct gga tgg tgc ggc    144
Ala Leu Cys Pro Asn Gly Leu Cys Cys Ser Glu Ala Gly Trp Cys Gly
            35                  40                  45 acc acc gaa gct tac tgc ggg cat ggt tgt caa agc cag tgc aat cct    192
Thr Thr Glu Ala Tyr Cys Gly His Gly Cys Gln Ser Gln Cys Asn Pro
        50                  55                  60 ggt ccc tat cct cct cct cca acc ccg cag tgt ggt cgt caa tcc ata    240
Gly Pro Tyr Pro Pro Pro Pro Thr Pro Gln Cys Gly Arg Gln Ser Ile
65                  70                  75 ccc gcg gga gcc ctc tgc ccc aac ggt cta tgc tgt agc gag gct gga    288
Pro Ala Gly Ala Leu Cys Pro Asn Gly Leu Cys Cys Ser Glu Ala Gly
80                  85                  90                  95 tgg tgc ggc acc acc gaa gct tac tgc ggg cat ggt tgc caa agc cag    336
Trp Cys Gly Thr Thr Glu Ala Tyr Cys Gly His Gly Cys Gln Ser Gln
                100                 105                 110 tgc act ccc att ccc act cct cct gct ccc act ccc act cct cct act    384
Cys Thr Pro Ile Pro Thr Pro Pro Ala Pro Thr Pro Thr Pro Pro Thr
            115                 120                 125 ccc act cct cct agt cct acc cct cct ggt ccc act cct cct ggt ccc    432
Pro Thr Pro Pro Ser Pro Thr Pro Pro Gly Pro Thr Pro Pro Gly Pro
        130                 135                 140 agc ggg gat ctt tct ggc atc att tca aga gat cag ttc tat aaa atg    480
Ser Gly Asp Leu Ser Gly Ile Ile Ser Arg Asp Gln Phe Tyr Lys Met
145                 150                 155
```

-continued

| | | |
|---|---|---|
| ctt aag cac atg aac gac aat gat tgt cat gct gtt ggt ttc ttc act<br>Leu Lys His Met Asn Asp Asn Asp Cys His Ala Val Gly Phe Phe Thr<br>160                         165                   170                175 | 528 |
| tac gac gcc ttc atc acc gcc gct aag tct ttc cca agt ttc ggg aac<br>Tyr Asp Ala Phe Ile Thr Ala Ala Lys Ser Phe Pro Ser Phe Gly Asn<br>                  180                   185                  190 | 576 |
| acc gga gac ctt gcc atg agg aag aag gag ata gca gcc ttc ttc ggc<br>Thr Gly Asp Leu Ala Met Arg Lys Lys Glu Ile Ala Ala Phe Phe Gly<br>195                         200                   205 | 624 |
| cag act tcc cac gaa acc acc ggt ggg tgg tcg ggt gca ccc gat gga<br>Gln Thr Ser His Glu Thr Thr Gly Gly Trp Ser Gly Ala Pro Asp Gly<br>                  210                   215                  220 | 672 |
| gca aat aca tgg ggc tac tgt tac aag gaa gaa att gac aaa agc gat<br>Ala Asn Thr Trp Gly Tyr Cys Tyr Lys Glu Glu Ile Asp Lys Ser Asp<br>225                         230                   235 | 720 |
| ccc cac tgt gat agc aac aac ctc gag tgg cca tgc gca cca ggc aaa<br>Pro His Cys Asp Ser Asn Asn Leu Glu Trp Pro Cys Ala Pro Gly Lys<br>240                         245                   250                  255 | 768 |
| ttt tac tac gga cga gga cca atg atg ctg tct tgg aac tat aat tac<br>Phe Tyr Tyr Gly Arg Gly Pro Met Met Leu Ser Trp Asn Tyr Asn Tyr<br>                  260                   265                  270 | 816 |
| gga ccg tgc ggg aga gac cta gga ctc gag tta ctc aag aac cca gat<br>Gly Pro Cys Gly Arg Asp Leu Gly Leu Glu Leu Leu Lys Asn Pro Asp<br>275                         280                   285 | 864 |
| gtt gcg tcc agc gac cca gtg ata gct ttc aaa acc gcc att tgg ttc<br>Val Ala Ser Ser Asp Pro Val Ile Ala Phe Lys Thr Ala Ile Trp Phe<br>                  290                   295                  300 | 912 |
| tgg atg act cct caa gct cct aaa ccc tcg tgc cac gac gtg atc acc<br>Trp Met Thr Pro Gln Ala Pro Lys Pro Ser Cys His Asp Val Ile Thr<br>305                         310                   315 | 960 |
| gac cag tgg gag ccg tcg gct gcc gac att tct gcc gga agg tta cca<br>Asp Gln Trp Glu Pro Ser Ala Ala Asp Ile Ser Ala Gly Arg Leu Pro<br>320                         325                   330                  335 | 1008 |
| ggt tat gga gtg att acc aat atc atc aac ggt gga tta gag tgt gct<br>Gly Tyr Gly Val Ile Thr Asn Ile Ile Asn Gly Gly Leu Glu Cys Ala<br>                  340                   345                  350 | 1056 |
| ggt cgc gac gtc gca aag gtc caa gat cgg ata tcg ttt tat aca agg<br>Gly Arg Asp Val Ala Lys Val Gln Asp Arg Ile Ser Phe Tyr Thr Arg<br>355                         360                   365 | 1104 |
| tac tgt ggc atg ttt ggt gtt gat cct gga agt aat att gac tgt gac<br>Tyr Cys Gly Met Phe Gly Val Asp Pro Gly Ser Asn Ile Asp Cys Asp<br>                  370                   375                  380 | 1152 |
| aat caa agg ccg ttt aat gaa ggt agt aac gtt ttc ttg gat gct gca<br>Asn Gln Arg Pro Phe Asn Glu Gly Ser Asn Val Phe Leu Asp Ala Ala<br>385                         390                   395 | 1200 |
| att taataagtac tgttaatgaa gctttgttgt atccaagcaa taagagagta<br>Ile<br>400 | 1253 |
| tcaaattaaa ttaataaaaa ctccttttta ttaagtaaaa aaaa | 1297 |

<210> SEQ ID NO 2
<211> LENGTH: 400
<212> TYPE: PRT
<213> ORGANISM: Brassica juncea

<400> SEQUENCE: 2

Met Lys Thr Tyr Leu Leu Leu Leu Ile Phe Ser Leu Leu Leu Ser
1                 5                    10                   15

Phe Ser Ser Gly Glu Gln Cys Gly Ser Gln Ser Ile Pro Glu Gly Ala

```
                    20                  25                  30
Leu Cys Pro Asn Gly Leu Cys Cys Ser Glu Ala Gly Trp Cys Gly Thr
            35                  40                  45

Thr Glu Ala Tyr Cys Gly His Gly Cys Gln Ser Gln Cys Asn Pro Gly
 50                  55                  60

Pro Tyr Pro Pro Pro Thr Pro Gln Cys Gly Arg Gln Ser Ile Pro
 65                  70                  75                  80

Ala Gly Ala Leu Cys Pro Asn Gly Leu Cys Cys Ser Glu Ala Gly Trp
                85                  90                  95

Cys Gly Thr Thr Glu Ala Tyr Cys Gly His Gly Cys Gln Ser Gln Cys
            100                 105                 110

Thr Pro Ile Pro Thr Pro Pro Ala Pro Thr Pro Thr Pro Pro Thr Pro
            115                 120                 125

Thr Pro Pro Ser Pro Thr Pro Pro Gly Pro Thr Pro Pro Gly Pro Ser
130                 135                 140

Gly Asp Leu Ser Gly Ile Ile Ser Arg Asp Gln Phe Tyr Lys Met Leu
145                 150                 155                 160

Lys His Met Asn Asp Asn Asp Cys His Ala Val Gly Phe Phe Thr Tyr
                165                 170                 175

Asp Ala Phe Ile Thr Ala Ala Lys Ser Phe Pro Ser Phe Gly Asn Thr
            180                 185                 190

Gly Asp Leu Ala Met Arg Lys Lys Glu Ile Ala Ala Phe Gly Gln
            195                 200                 205

Thr Ser His Glu Thr Thr Gly Gly Trp Ser Gly Ala Pro Asp Gly Ala
210                 215                 220

Asn Thr Trp Gly Tyr Cys Tyr Lys Glu Glu Ile Asp Lys Ser Asp Pro
225                 230                 235                 240

His Cys Asp Ser Asn Asn Leu Glu Trp Pro Cys Ala Pro Gly Lys Phe
                245                 250                 255

Tyr Tyr Gly Arg Gly Pro Met Met Leu Ser Trp Asn Tyr Asn Tyr Gly
                260                 265                 270

Pro Cys Gly Arg Asp Leu Gly Leu Glu Leu Leu Lys Asn Pro Asp Val
            275                 280                 285

Ala Ser Ser Asp Pro Val Ile Ala Phe Lys Thr Ala Ile Trp Phe Trp
290                 295                 300

Met Thr Pro Gln Ala Pro Lys Pro Ser Cys His Asp Val Ile Thr Asp
305                 310                 315                 320

Gln Trp Glu Pro Ser Ala Ala Asp Ile Ser Ala Gly Arg Leu Pro Gly
                325                 330                 335

Tyr Gly Val Ile Thr Asn Ile Ile Asn Gly Gly Leu Glu Cys Ala Gly
            340                 345                 350

Arg Asp Val Ala Lys Val Gln Asp Arg Ile Ser Phe Tyr Thr Arg Tyr
            355                 360                 365

Cys Gly Met Phe Gly Val Asp Pro Gly Ser Asn Ile Asp Cys Asp Asn
            370                 375                 380

Gln Arg Pro Phe Asn Glu Gly Ser Asn Val Phe Leu Asp Ala Ala Ile
385                 390                 395                 400

<210> SEQ ID NO 3
<211> LENGTH: 1242
<212> TYPE: DNA
<213> ORGANISM: Hevea brasiliensis

<400> SEQUENCE: 3
```

-continued

```
aaattataag caactttctt ctaatttccc cccttcttaa tggctatctc ctcttcaact      60
tcaggaacta gtagttcctt ccctcaaga actactgtca tgcttcttct gttttcttt       120 gcagcaagcg ttggtataac agatgcccag gtaggtgttt gctatggaat gcaaggcaac     180
aaccttccac ctgtttcaga ggtcatagct ctctataaaa atctaacat cacgagaatg      240 agaatttatg atccaaatcg agcagtattg gaagccctta gaggctcaaa cattgaactc     300
atactaggtg ttccaaactc agatctccaa agccttacca atccttccaa tgcaaaatca    360
tgggtacaaa aaatgttcg tggcttctgg tcaagtgtcc tgttcagata tatagcagtt     420
ggcaacgaaa ttagtcctgt caatagaggc acagcttggt tggctcaatt tgttttgcct    480
gccatgagaa atatacatga tgctataaga tcagctggtc ttcaagatca aatcaaggtc    540
tccactgcaa ttgacttgac cctggtagga aattcctacc ctccttctgc aggtgctttc    600
agggatgatg ttagatcata cttggaccca attattggat ttctatcctc tatcaggtca   660
cctttacttg ccaatattta tccttacttt acttatgctt ataatccaag ggatatttcc    720
cttccctatg ctttgttcac ttcaccatca gttgttgtgt gggatggtca gcgaggttat    780
aagaaccttt tgatgcaac gttggatgca ttgtactctg ctcttgagag ggctagtggt     840
ggttctctgg aggtggttgt ttcggaaagt ggctggccgt ctgccggagc atttgctgcc    900
acatttgaca atgggcgtac ttatctctca aatttgatcc aacatgttaa aggaggtact   960
cctaagaggc ctaacagagc tatagagact tacttatttg ccatgtttga tgaaaataag  1020
aagcaaccag aggttgagaa acactttgga cttttctttc ctgataaacg gccaaaatat  1080
aatctcaatt ttggtgcaga aaagaactgg gatatttcta ctgaacacaa tgcaacaata  1140
cttttcctta agagtgatat gtgagattgt gagaatttaa gtactatata tatttccaat  1200
gtatgcatgt atccatgtat taaataagag aaccttttct ca                     1242
```

<210> SEQ ID NO 4
<211> LENGTH: 374
<212> TYPE: PRT
<213> ORGANISM: Hevea brasiliensis

<400> SEQUENCE: 4

```
Met Ala Ile Ser Ser Thr Ser Gly Thr Ser Ser Ser Phe Pro Ser
  1               5                  10                  15

Arg Thr Thr Val Met Leu Leu Leu Phe Phe Ala Ala Ser Val Gly
                 20                  25                  30

Ile Thr Asp Ala Gln Val Gly Val Cys Tyr Gly Met Gln Gly Asn Asn
                 35                  40                  45

Leu Pro Pro Val Ser Glu Val Ile Ala Leu Tyr Lys Lys Ser Asn Ile
 50                  55                  60

Thr Arg Met Arg Ile Tyr Asp Pro Asn Arg Ala Val Leu Glu Ala Leu
 65                  70                  75                  80

Arg Gly Ser Asn Ile Glu Leu Ile Leu Gly Val Pro Asn Ser Asp Leu
                 85                  90                  95

Gln Ser Leu Thr Asn Pro Ser Asn Ala Lys Ser Trp Val Gln Lys Asn
                100                 105                 110

Val Arg Gly Phe Trp Ser Ser Val Leu Phe Arg Tyr Ile Ala Val Gly
                115                 120                 125

Asn Glu Ile Ser Pro Val Asn Arg Gly Thr Ala Trp Leu Ala Gln Phe
                130                 135                 140

Val Leu Pro Ala Met Arg Asn Ile His Asp Ala Ile Arg Ser Ala Gly
145                 150                 155                 160
```

```
Leu Gln Asp Gln Ile Lys Val Ser Thr Ala Ile Asp Leu Thr Leu Val
                165                 170                 175
Gly Asn Ser Tyr Pro Pro Ser Ala Gly Ala Phe Arg Asp Asp Val Arg
            180                 185                 190
Ser Tyr Leu Asp Pro Ile Ile Gly Phe Leu Ser Ser Ile Arg Ser Pro
        195                 200                 205
Leu Leu Ala Asn Ile Tyr Pro Tyr Phe Thr Tyr Ala Tyr Asn Pro Arg
    210                 215                 220
Asp Ile Ser Leu Pro Tyr Ala Leu Phe Thr Ser Pro Ser Val Val Val
225                 230                 235                 240
Trp Asp Gly Gln Arg Gly Tyr Lys Asn Leu Phe Asp Ala Thr Leu Asp
                245                 250                 255
Ala Leu Tyr Ser Ala Leu Glu Arg Ala Ser Gly Ser Leu Glu Val
            260                 265                 270
Val Val Ser Glu Ser Gly Trp Pro Ser Ala Gly Ala Phe Ala Ala Thr
        275                 280                 285
Phe Asp Asn Gly Arg Thr Tyr Leu Ser Asn Leu Ile Gln His Val Lys
    290                 295                 300
Gly Gly Thr Pro Lys Arg Pro Asn Arg Ala Ile Glu Thr Tyr Leu Phe
305                 310                 315                 320
Ala Met Phe Asp Glu Asn Lys Lys Gln Pro Glu Val Glu Lys His Phe
                325                 330                 335
Gly Leu Phe Phe Pro Asp Lys Arg Pro Lys Tyr Asn Leu Asn Phe Gly
            340                 345                 350
Ala Glu Lys Asn Trp Asp Ile Ser Thr Glu His Asn Ala Thr Ile Leu
        355                 360                 365
Phe Leu Lys Ser Asp Met
    370

<210> SEQ ID NO 5
<211> LENGTH: 27
<212> TYPE: DNA
<213> ORGANISM: Artificial
<220> FEATURE:
<223> OTHER INFORMATION: Description of Artificial Sequence:
      C1(forward)primer

<400> SEQUENCE: 5
ctgaattctc ctccggtgag caatgcg                                    27

<210> SEQ ID NO 6
<211> LENGTH: 26
<212> TYPE: DNA
<213> ORGANISM: Artificial
<220> FEATURE:
<223> OTHER INFORMATION: Description of Artificial Sequence:
      C21(forward)primer

<400> SEQUENCE: 6
ctgaattcgg ggatctttct ggcatc                                     26

<210> SEQ ID NO 7
<211> LENGTH: 34
<212> TYPE: DNA
<213> ORGANISM: Artificial
<220> FEATURE:
<223> OTHER INFORMATION: Description of Artificial Sequence:
      C2(reverse)primer

<400> SEQUENCE: 7
```

```
gcgactgcgg ccgcgttact accttcatta aacg                    34
```

<210> SEQ ID NO 8
<211> LENGTH: 12
<212> TYPE: PRT
<213> ORGANISM: Brassica juncea
<220> FEATURE:
<223> OTHER INFORMATION: the peptide corresponds to amino acid
      residues 231 to 242 of BjCHI1

<400> SEQUENCE: 8

Tyr Lys Glu Glu Ile Asp Lys Ser Asp Pro His Cys
 1               5                  10

<210> SEQ ID NO 9
<211> LENGTH: 5
<212> TYPE: PRT
<213> ORGANISM: Brassica juncea
<220> FEATURE:
<223> OTHER INFORMATION: the peptide corresponds to amino acid
      residues 268 to 272 of BjCHI1

<400> SEQUENCE: 9

Asn Tyr Asn Tyr Gly
 1               5

<210> SEQ ID NO 10
<211> LENGTH: 24
<212> TYPE: DNA
<213> ORGANISM: Artificial Sequence
<220> FEATURE:
<223> OTHER INFORMATION: Primer for PCR amplification of Arabidopsis
      chitinase gene (nucleotides 1625-2038)

<400> SEQUENCE: 10

```
ggtggatggg ctacagcacc agac                               24
```

<210> SEQ ID NO 11
<211> LENGTH: 18
<212> TYPE: DNA
<213> ORGANISM: Artificial Sequence
<220> FEATURE:
<223> OTHER INFORMATION: Primer for PCR amplification of Arabidopsis
      chitinase gene (nucleotides 1625-2038)

<400> SEQUENCE: 11

```
gccacgtcca cactccaa                                      18
```

<210> SEQ ID NO 12
<211> LENGTH: 18
<212> TYPE: DNA
<213> ORGANISM: Artificial Sequence
<220> FEATURE:
<223> OTHER INFORMATION: Primer P1 for PCR amplification of BjCHI1

<400> SEQUENCE: 12

```
cctccggtga gcaatgcg                                      18
```

<210> SEQ ID NO 13
<211> LENGTH: 19
<212> TYPE: DNA
<213> ORGANISM: Artificial Sequence
<220> FEATURE:
<223> OTHER INFORMATION: Primer P2 for PCR amplification of BjCHI1

<400> SEQUENCE: 13

-continued ttagcggcgg tgatgaagg                                                    19

<210> SEQ ID NO 14
<211> LENGTH: 19
<212> TYPE: DNA
<213> ORGANISM: Artificial Sequence
<220> FEATURE:
<223> OTHER INFORMATION: Primer P3 for PCR amplification of BjCHI1

<400> SEQUENCE: 14
tcctccaacc ccgcagtgt                                                    19

<210> SEQ ID NO 15
<211> LENGTH: 17
<212> TYPE: DNA
<213> ORGANISM: Artificial Sequence
<220> FEATURE:
<223> OTHER INFORMATION: Primer P4 for PCR amplification of BjCHI1

<400> SEQUENCE: 15
ccactcgagg ttgttgc                                                      17

<210> SEQ ID NO 16
<211> LENGTH: 14
<212> TYPE: PRT
<213> ORGANISM: Hevea brasiliensis
<220> FEATURE:
<223> OTHER INFORMATION: the peptide corresponds to amino acid
      residues 94 to 107 of HbGLU

<400> SEQUENCE: 16

Ser Asp Leu Gln Ser Leu Thr Asn Pro Ser Asn Ala Lys Ser
  1               5                  10

<210> SEQ ID NO 17
<211> LENGTH: 329
<212> TYPE: PRT
<213> ORGANISM: Nicotiana tabacum

<400> SEQUENCE: 17

Met Arg Leu Cys Lys Phe Thr Ala Leu Ser Ser Leu Leu Phe Ser Leu
  1               5                  10                  15

Leu Leu Leu Ser Ala Ser Ala Glu Gln Cys Gly Ser Gln Ala Gly Gly
             20                  25                  30

Ala Arg Cys Pro Ser Gly Leu Cys Cys Ser Lys Phe Gly Trp Cys Gly
         35                  40                  45

Asn Thr Asn Asp Tyr Cys Gly Pro Gly Asn Cys Gln Ser Gln Cys Pro
     50                  55                  60

Gly Gly Pro Thr Pro Thr Pro Thr Pro Pro Gly Gly Gly Asp Leu
 65                  70                  75                  80

Gly Ser Ile Ile Ser Ser Ser Met Phe Asp Gln Met Leu Lys His Arg
                 85                  90                  95

Asn Asp Asn Ala Cys Gln Gly Lys Gly Phe Tyr Ser Tyr Asn Ala Phe
            100                 105                 110

Ile Asn Ala Ala Arg Ser Phe Pro Gly Phe Gly Thr Ser Gly Asp Thr
        115                 120                 125

Thr Ala Arg Lys Arg Glu Ile Ala Ala Phe Phe Ala Gln Thr Ser His
    130                 135                 140

Glu Thr Thr Gly Gly Trp Ala Thr Ala Pro Asp Gly Pro Tyr Ala Trp
145                 150                 155                 160

Gly Tyr Cys Trp Leu Arg Glu Gln Gly Ser Pro Gly Asp Tyr Cys Thr

-continued

```
                165                 170                 175
Pro Ser Gly Gln Trp Pro Cys Ala Pro Gly Arg Lys Tyr Phe Gly Arg
            180                 185                 190

Gly Pro Ile Gln Ile Ser His Asn Tyr Asn Tyr Gly Pro Cys Gly Arg
        195                 200                 205

Ala Ile Gly Val Asp Leu Leu Asn Asn Pro Asp Leu Val Ala Thr Asp
    210                 215                 220

Pro Val Ile Ser Phe Lys Ser Ala Leu Trp Phe Trp Met Thr Pro Gln
225                 230                 235                 240

Ser Pro Lys Pro Ser Cys His Asp Val Ile Gly Arg Trp Gln Pro
                245                 250                 255

Ser Ala Gly Asp Arg Ala Ala Asn Arg Leu Pro Gly Phe Gly Val Ile
            260                 265                 270

Thr Asn Ile Ile Asn Gly Gly Leu Glu Cys Gly Arg Gly Thr Asp Ser
        275                 280                 285

Arg Val Gln Asp Arg Ile Gly Phe Tyr Arg Arg Tyr Cys Ser Ile Leu
    290                 295                 300

Gly Val Ser Pro Gly Asp Asn Leu Asp Cys Gly Asn Gln Arg Ser Phe
305                 310                 315                 320

Gly Asn Gly Leu Leu Val Asp Thr Met
                325
```

<210> SEQ ID NO 18
<211> LENGTH: 253
<212> TYPE: PRT
<213> ORGANISM: Nicotiana tabacum

<400> SEQUENCE: 18

```
Met Glu Phe Ser Gly Ser Pro Met Ala Leu Phe Cys Cys Val Phe Phe
1               5                   10                  15

Leu Phe Leu Thr Gly Ser Leu Ala Gln Gly Ile Gly Ser Ile Val Thr
            20                  25                  30

Ser Asp Leu Phe Asn Glu Met Leu Lys Asn Arg Asn Asp Gly Arg Cys
        35                  40                  45

Pro Ala Asn Gly Phe Tyr Thr Tyr Asp Ala Phe Ile Ala Ala Ala Asn
    50                  55                  60

Ser Phe Pro Gly Phe Gly Thr Thr Gly Asp Asp Thr Ala Arg Arg Lys
65                  70                  75                  80

Glu Ile Ala Ala Phe Phe Gly Gln Thr Ser His Glu Thr Thr Gly Gly
                85                  90                  95

Ser Leu Ser Ala Glu Pro Phe Thr Gly Gly Tyr Cys Phe Val Arg Gln
            100                 105                 110

Asn Asp Gln Ser Asp Arg Tyr Tyr Gly Arg Gly Pro Ile Gln Leu Thr
        115                 120                 125

Asn Arg Asn Asn Tyr Glu Lys Ala Gly Thr Ala Ile Gly Gln Glu Leu
    130                 135                 140

Val Asn Asn Pro Asp Leu Val Ala Thr Asp Ala Thr Ile Ser Phe Lys
145                 150                 155                 160

Thr Ala Ile Trp Phe Trp Met Thr Pro Gln Asp Asn Lys Pro Ser Ser
                165                 170                 175

His Asp Val Ile Ile Gly Arg Trp Thr Pro Ser Ala Ala Asp Gln Ala
            180                 185                 190

Ala Asn Arg Val Pro Gly Tyr Gly Val Ile Thr Asn Ile Ile Asn Gly
        195                 200                 205
```

```
Gly Ile Glu Cys Gly Ile Gly Arg Asn Asp Ala Val Glu Asp Arg Ile
    210                 215                 220

Gly Tyr Tyr Arg Arg Tyr Cys Gly Met Leu Asn Val Ala Pro Gly Glu
225                 230                 235                 240

Asn Leu Asp Cys Tyr Asn Gln Arg Asn Phe Gly Gln Gly
                245                 250

<210> SEQ ID NO 19
<211> LENGTH: 270
<212> TYPE: PRT
<213> ORGANISM: Phaseolus vulgaris

<400> SEQUENCE: 19

Met Gly Asn Lys Leu Val Leu Val Leu Val Ala Val Ala Leu Val Met
  1               5                  10                  15

Gly Pro Lys Asn Val Ser Ala Gln Asn Cys Gly Cys Ala Glu Gly Leu
                 20                  25                  30

Cys Cys Ser Gln Tyr Gly Tyr Cys Gly Thr Gly Glu Asp Tyr Cys Gly
             35                  40                  45

Thr Gly Cys Gln Gln Gly Pro Cys Thr Thr Ala Ser Pro Pro Pro Ser
         50                  55                  60

Asn Asn Val Asn Ala Asp Ile Leu Thr Ala Asp Phe Leu Asn Gly Ile
 65                  70                  75                  80

Ile Asp Gln Ala Asp Ser Gly Cys Ala Gly Lys Asn Phe Tyr Thr Arg
                 85                  90                  95

Asp Ala Phe Leu Ser Ala Leu Asn Ser Tyr Thr Asp Phe Gly Arg Val
            100                 105                 110

Gly Ser Glu Asp Asp Ser Lys Arg Glu Ile Ala Ala Ala Phe Ala His
        115                 120                 125

Phe Thr His Glu Thr Gly His Phe Cys Tyr Ile Glu Glu Ile Asp Gly
130                 135                 140

Ala Ser Lys Asp Tyr Cys Asp Glu Glu Ser Ile Ala Gln Tyr Pro Cys
145                 150                 155                 160

Ser Ser Ser Lys Gly Tyr His Gly Arg Gly Pro Ile Gln Leu Ser Trp
                165                 170                 175

Asn Phe Asn Tyr Gly Pro Ala Gly Ser Ala Asn Asn Phe Asp Gly Leu
            180                 185                 190

Gly Ala Pro Glu Thr Val Ser Asn Asp Val Val Ser Phe Lys Thr
        195                 200                 205

Ala Leu Trp Tyr Trp Met Gln His Val Arg Pro Val Ile Asn Gln Gly
    210                 215                 220

Phe Gly Ala Thr Ile Arg Ala Ile Asn Gly Ala Leu Glu Cys Asp Gly
225                 230                 235                 240

Ala Asn Pro Thr Thr Val Gln Ala Arg Val Asn Tyr Tyr Thr Glu Tyr
                245                 250                 255

Cys Arg Gln Leu Gly Val Ala Thr Gly Asp Asn Leu Thr Cys
            260                 265                 270

<210> SEQ ID NO 20
<211> LENGTH: 372
<212> TYPE: PRT
<213> ORGANISM: Urtica dioica

<400> SEQUENCE: 20

Met Met Met Arg Phe Leu Ser Ala Val Val Ile Met Ser Ser Ala Met
  1               5                  10                  15
```

-continued

```
Ala Val Gly Leu Val Ser Ala Gln Arg Cys Gly Ser Gln Gly Gly
            20                  25                  30

Gly Thr Cys Pro Ala Leu Trp Cys Ser Ile Trp Gly Trp Cys Gly
            35                  40                  45

Asp Ser Glu Pro Tyr Cys Gly Arg Thr Cys Glu Asn Lys Cys Trp Ser
            50                  55                  60

Gly Glu Arg Ser Asp His Arg Cys Gly Ala Ala Val Gly Asn Pro Pro
 65                  70                  75                  80

Cys Gly Gln Asp Arg Cys Cys Ser Val His Gly Trp Cys Gly Gly
                85                  90                  95

Asn Asp Tyr Cys Ser Gly Ser Lys Cys Gln Tyr Arg Cys Ser Ser
            100                 105                 110

Val Arg Gly Pro Arg Val Ala Leu Ser Gly Asn Ser Thr Ala Asn Ser
            115                 120                 125

Ile Gly Asn Val Val Thr Glu Pro Leu Phe Asp Gln Met Phe Ser
 130                 135                 140

His Arg Lys Asp Cys Pro Ser Gln Gly Phe Tyr Ser Tyr His Ser Phe
 145                 150                 155                 160

Leu Val Ala Ala Glu Ser Phe Pro Ala Phe Gly Thr Ile Gly Asp Val
            165                 170                 175

Ala Thr Arg Lys Arg Glu Val Ala Ala Phe Leu Ala His Ile Ser Gln
            180                 185                 190

Ala Thr Ser Gly Glu Arg Ser Asp Val Glu Asn Pro His Ala Trp Gly
            195                 200                 205

Leu Cys His Ile Asn Thr Thr Thr Val Thr Glu Asn Asp Phe Cys Thr
 210                 215                 220

Ser Ser Asp Trp Pro Cys Ala Ala Gly Lys Lys Tyr Ser Pro Arg Gly
225                 230                 235                 240

Pro Ile Gln Leu Thr His Asn Phe Asn Tyr Gly Leu Ala Gly Gln Ala
            245                 250                 255

Ile Gly Glu Asp Leu Ile Gln Asn Pro Asp Leu Val Glu Lys Asp Pro
            260                 265                 270

Ile Ile Ser Phe Lys Thr Ala Leu Trp Phe Trp Met Ser Gln His Asp
            275                 280                 285

Asn Lys Pro Ser Cys His Asp Ile Val Leu Asn Ala Asn Ser Ala Ala
 290                 295                 300

Asn Arg Ile Pro Asn Lys Gly Val Ile Gly Asn Ile Ser Arg Ala
305                 310                 315                 320

Phe Gly His Asp Asp Phe Ala Val Arg Ser Ser Ile Gly Phe Tyr
            325                 330                 335

Lys Arg Tyr Cys Asp Met Leu Gly Val Ser Tyr Gly His Asp Leu Lys
            340                 345                 350

Tyr Trp Phe Asp Asn Thr Pro Ser Ser Glu Phe Gln Arg Ile Gln Met
            355                 360                 365

Arg Val Ala Ala
370
```

<210> SEQ ID NO 21
<211> LENGTH: 439
<212> TYPE: PRT
<213> ORGANISM: Beta vulgaris

<400> SEQUENCE: 21

```
Met Lys Ile Lys Thr Ser Pro Ser Phe Leu Leu Gly Leu Ile Cys Leu
 1               5                  10                  15
```

```
Ala Leu Val Leu Leu Gly Glu Gly Val Gln Cys Gly Arg Gln Cys
         20                  25                  30

Asn Thr Thr Asp Thr Asn Cys Leu Ser Gly Cys Ser Val Gly Arg Pro
         35                  40                  45

Ser Arg Pro Thr Pro Pro Arg Pro Pro Thr Pro Arg Pro Pro Pro Pro
     50                  55                  60

Arg Pro Pro Thr Pro Arg Pro Pro Pro Arg Pro Pro Thr Pro Arg
 65                  70                  75                  80

Pro Pro Pro Pro Thr Pro Arg Pro Pro Pro Arg Pro Pro Thr Pro
                 85                  90                  95

Arg Pro Pro Pro Pro Thr Pro Arg Pro Pro Pro Arg Pro Pro
                100                 105                 110

Thr Pro Arg Pro Pro Pro Pro Thr Pro Arg Pro Pro Pro Pro
             115                 120                 125

Thr Pro Arg Pro Pro Pro Ser Pro Pro Thr Pro Arg Pro Pro Pro
             130                 135                 140

Pro Pro Pro Pro Ser Pro Pro Thr Pro Ser Pro Pro Ser Pro Pro Ser
145                 150                 155                 160

Pro Glu Pro Pro Thr Pro Pro Glu Pro Thr Pro Pro Thr Pro Thr Pro
                 165                 170                 175

Pro Thr His Leu Thr Asp Ile Ile Ser Glu Glu Met Phe Asn Glu Phe
             180                 185                 190

Leu Leu Asn Arg Ile Gln Pro Arg Cys Pro Gly Arg Trp Phe Tyr Thr
             195                 200                 205

Tyr Gln Ala Phe Ile Thr Ala Ala Glu Thr Phe Pro Glu Phe Gly Asn
     210                 215                 220

Thr Gly Asn Asp Glu Ile Arg Lys Arg Glu Ile Ala Ala Phe Phe Gly
225                 230                 235                 240

Gln Thr Ser His Glu Thr Ser Gly Glu Pro Thr Ala Gln His Gly Pro
                 245                 250                 255

Phe Thr Trp Gly Tyr Cys Phe Ile Glu Glu Ile Gly Ala Gly Pro Leu
             260                 265                 270

Ser Gln Tyr Cys Ala Pro Ser Val Glu Trp Pro Cys Ile Arg Gly Arg
     275                 280                 285

Phe Tyr Tyr Gly Arg Gly Pro Val Gln Leu Thr Trp Asn Phe Asn Tyr
     290                 295                 300

Gly Lys Gln Val Lys His Leu Gly Leu Asp Leu Leu Phe Asn Pro Asp
305                 310                 315                 320

Ile Val Ala His Asp Pro Val Ile Ser Phe Glu Thr Ala Ile Trp Phe
                 325                 330                 335

Trp Met Thr Pro Glu Gly Asn Lys Pro Ser Ser His Glu Val Ile Thr
             340                 345                 350

Gly Gln Trp Thr Pro Thr Pro Ala Asp Ile Ala Arg Asn Arg Leu Pro
             355                 360                 365

Gly Tyr Gly Leu Ile Thr Asn Ile Phe Asn Gly Ala Leu Glu Cys Gly
     370                 375                 380

Thr His Gly Pro Asp Asn Arg Gly Glu Asn Arg Ile Gln Phe Tyr Gln
385                 390                 395                 400

Arg Tyr Cys Asp Leu Leu Asp Val Ser Tyr Gly Asp Asn Leu Asp Cys
                 405                 410                 415

Tyr Arg Gln Thr Pro Phe Asp Trp Gly Leu Lys Lys Leu Gln Gly Ala
             420                 425                 430
```

-continued

Arg Glu Ser Trp Ser Ser Ser
        435

<210> SEQ ID NO 22
<211> LENGTH: 370
<212> TYPE: PRT
<213> ORGANISM: Nicotiana plumbaginifolia

<400> SEQUENCE: 22

Met Asp Thr Ser His Lys His Ile Ala Leu Gln Met Ala Ala Ile Ile
 1               5                  10                  15

Leu Leu Gly Leu Leu Val Ser Ser Thr Glu Ile Val Gly Ala Gln Ser
            20                  25                  30

Val Gly Val Cys Tyr Gly Met Leu Gly Asn Asn Leu Pro Pro Ala Ser
        35                  40                  45

Gln Val Val Gln Leu Tyr Lys Ser Lys Asn Ile Arg Arg Met Arg Leu
    50                  55                  60

Tyr Asp Pro Asn Gln Ala Ala Leu Gln Ala Leu Arg Gly Ser Asn Ile
 65                  70                  75                  80

Glu Val Met Leu Gly Val Pro Asn Ser Asp Leu Gln Asn Ile Ala Ala
                85                  90                  95

Asn Pro Ser Asn Ala Asn Asn Trp Val Gln Arg Asn Val Arg Asn Phe
            100                 105                 110

Trp Pro Ala Val Lys Phe Arg Tyr Ile Ala Val Gly Asn Glu Val Ser
        115                 120                 125

Pro Val Thr Gly Thr Ser Ser Leu Thr Arg Tyr Leu Leu Pro Ala Met
    130                 135                 140

Arg Asn Ile Arg Asn Ala Ile Ser Ser Ala Gly Leu Gln Asn Asn Ile
145                 150                 155                 160

Lys Val Ser Ser Val Asp Met Thr Leu Ile Gly Asn Ser Phe Pro
                165                 170                 175

Pro Ser Gln Gly Ser Phe Arg Asn Asp Val Arg Ser Phe Ile Asp Pro
            180                 185                 190

Ile Ile Gly Phe Val Arg Arg Ile Asn Ser Pro Leu Leu Val Asn Ile
        195                 200                 205

Tyr Pro Tyr Phe Ser Tyr Ala Gly Asn Pro Arg Asp Ile Ser Leu Pro
    210                 215                 220

Tyr Ala Leu Phe Thr Ala Pro Asn Val Val Gln Asp Gly Ser Leu
225                 230                 235                 240

Gly Tyr Arg Asn Leu Phe Asp Ala Met Ser Asp Ala Val Tyr Ala Ala
                245                 250                 255

Leu Ser Arg Ala Gly Gly Gly Ser Ile Glu Ile Val Val Ser Glu Ser
            260                 265                 270

Gly Trp Pro Ser Ala Gly Ala Phe Ala Ala Thr Thr Asn Asn Ala Ala
        275                 280                 285

Thr Tyr Tyr Lys Asn Leu Ile Gln His Val Lys Arg Gly Ser Pro Arg
    290                 295                 300

Arg Pro Asn Lys Val Ile Glu Thr Tyr Leu Phe Ala Met Phe Asp Glu
305                 310                 315                 320

Asn Asn Lys Asn Pro Glu Leu Glu Lys His Phe Gly Leu Phe Ser Pro
                325                 330                 335

Asn Lys Gln Pro Lys Tyr Pro Leu Ser Phe Gly Phe Ser Asp Arg Tyr
            340                 345                 350

Trp Asp Ile Ser Ala Glu Asn Asn Ala Thr Ala Ala Ser Leu Ile Ser
        355                 360                 365

```
Glu Met
    370

<210> SEQ ID NO 23
<211> LENGTH: 343
<212> TYPE: PRT
<213> ORGANISM: Nicotiana tabacum

<400> SEQUENCE: 23

Met Thr Leu Cys Ile Lys Asn Gly Phe Leu Ala Ala Leu Val Leu
  1               5                  10                  15

Val Gly Leu Leu Ile Cys Ser Ile Gln Met Ile Gly Ala Gln Ser Ile
                 20                  25                  30

Gly Val Cys Tyr Gly Lys His Ala Asn Asn Leu Pro Ser Asp Gln Asp
             35                  40                  45

Val Ile Asn Leu Tyr Asn Ala Asn Gly Ile Arg Lys Met Arg Ile Tyr
         50                  55                  60

Asn Pro Asp Thr Asn Val Phe Asn Ala Leu Arg Gly Ser Asn Ile Glu
 65                  70                  75                  80

Ile Ile Leu Asp Val Pro Leu Gln Asp Leu Gln Ser Leu Thr Asp Pro
                 85                  90                  95

Ser Arg Ala Asn Gly Trp Val Gln Asp Asn Ile Ile Asn His Phe Pro
            100                 105                 110

Asp Val Lys Phe Lys Tyr Ile Ala Val Gly Asn Glu Val Ser Pro Gly
        115                 120                 125

Asn Asn Gly Gln Tyr Ala Pro Phe Val Ala Pro Ala Met Gln Asn Val
    130                 135                 140

Tyr Asn Ala Leu Ala Ala Gly Leu Gln Asp Gln Ile Lys Val Ser
145                 150                 155                 160

Thr Ala Thr Tyr Ser Gly Ile Leu Ala Asn Thr Tyr Pro Pro Lys Asp
                165                 170                 175

Ser Ile Phe Arg Gly Glu Phe Asn Ser Phe Ile Asn Pro Ile Ile Gln
            180                 185                 190

Phe Leu Val Gln His Asn Leu Pro Leu Leu Ala Asn Val Tyr Pro Tyr
        195                 200                 205

Phe Gly His Ile Phe Asn Thr Ala Asp Val Pro Leu Ser Tyr Ala Leu
    210                 215                 220

Phe Thr Gln Gln Glu Ala Asn Pro Ala Gly Tyr Gln Asn Leu Phe Asp
225                 230                 235                 240

Ala Leu Leu Asp Ser Met Tyr Phe Ala Val Glu Lys Ala Gly Gly Gln
                245                 250                 255

Asn Val Glu Ile Ile Val Ser Glu Ser Gly Trp Pro Ser Glu Gly Asn
            260                 265                 270

Ser Ala Ala Thr Ile Glu Asn Ala Gln Thr Tyr Tyr Glu Asn Leu Ile
        275                 280                 285

Asn His Val Lys Ser Gly Ala Gly Thr Pro Lys Lys Pro Gly Lys Ala
    290                 295                 300

Ile Glu Thr Tyr Leu Phe Ala Met Phe Asp Glu Asn Asn Lys Glu Gly
305                 310                 315                 320

Asp Ile Thr Glu Lys His Phe Gly Leu Phe Ser Pro Asp Gln Arg Ala
                325                 330                 335

Lys Tyr Gln Leu Asn Phe Asn
            340
```

-continued

```
<210> SEQ ID NO 24
<211> LENGTH: 339
<212> TYPE: PRT
<213> ORGANISM: Nicotiana tabacum

<400> SEQUENCE: 24
```

Met Ala His Leu Ile Val Thr Leu Leu Leu Ser Val Leu Thr Leu
 1               5                  10                  15

Ala Thr Leu Asp Phe Thr Gly Ala Gln Ala Gly Val Cys Tyr Gly Arg
            20                  25                  30

Gln Gly Asn Gly Leu Pro Ser Pro Ala Asp Val Val Ser Leu Cys Asn
        35                  40                  45

Arg Asn Asn Ile Arg Arg Met Arg Ile Tyr Asp Pro Asp Gln Pro Thr
    50                  55                  60

Leu Glu Ala Leu Arg Gly Ser Asn Ile Glu Leu Met Leu Gly Val Pro
65                  70                  75                  80

Asn Pro Asp Leu Glu Asn Val Ala Ala Ser Gln Ala Asn Ala Asp Thr
                85                  90                  95

Trp Val Gln Asn Asn Val Arg Asn Tyr Gly Asn Val Lys Phe Arg Tyr
            100                 105                 110

Ile Ala Val Gly Asn Glu Val Ser Pro Leu Asn Glu Asn Ser Lys Tyr
        115                 120                 125

Val Pro Val Leu Leu Asn Ala Met Arg Asn Ile Gln Thr Ala Ile Ser
    130                 135                 140

Gly Ala Gly Leu Gly Asn Gln Ile Lys Val Ser Thr Ala Ile Glu Thr
145                 150                 155                 160

Gly Leu Thr Thr Asp Thr Ser Pro Pro Ser Asn Gly Arg Phe Lys Asp
                165                 170                 175

Asp Val Arg Gln Phe Ile Glu Pro Ile Ile Asn Phe Leu Val Thr Asn
            180                 185                 190

Arg Ala Pro Leu Leu Val Asn Leu Tyr Pro Tyr Phe Ala Ile Ala Asn
        195                 200                 205

Asn Ala Asp Ile Lys Leu Glu Tyr Ala Leu Phe Thr Ser Ser Glu Val
    210                 215                 220

Val Val Asn Asp Asn Gly Arg Gly Tyr Arg Asn Leu Phe Asp Ala Ile
225                 230                 235                 240

Leu Asp Ala Thr Tyr Ser Ala Leu Glu Lys Ala Ser Gly Ser Ser Leu
                245                 250                 255

Glu Ile Val Val Ser Glu Ser Gly Trp Pro Ser Ala Gly Ala Gly Gln
            260                 265                 270

Leu Thr Ser Ile Asp Asn Ala Arg Thr Tyr Asn Asn Asn Leu Ile Ser
        275                 280                 285

His Val Lys Gly Gly Ser Pro Lys Arg Pro Ser Gly Pro Ile Glu Thr
    290                 295                 300

Tyr Val Phe Ala Leu Phe Asp Glu Asp Gln Lys Asp Pro Glu Ile Glu
305                 310                 315                 320

Lys His Phe Gly Leu Phe Ser Ala Asn Met Gln Pro Lys Tyr Gln Ile
                325                 330                 335

Ser Phe Asn

```
<210> SEQ ID NO 25
<211> LENGTH: 349
<212> TYPE: PRT
<213> ORGANISM: Nicotiana tabacum

<400> SEQUENCE: 25
```

-continued

```
Met Ala Leu Trp Tyr Leu Phe Asn Lys Arg Ser Leu Gly Ala Ala Val
 1           5                  10                  15

Leu Ile Leu Val Gly Leu Leu Met Cys Asn Ile Gln Met Thr Gly Ala
             20                  25                  30

Gln Ser Asn Ile Gly Val Cys Tyr Gly Lys Ile Ala Asn Asn Leu Pro
         35                  40                  45

Ser Glu Gln Asp Val Ile Asn Leu Tyr Lys Ala Asn Gly Ile Arg Lys
     50                  55                  60

Met Arg Ile Tyr Asn Ser Asp Thr Asn Ile Phe Lys Ser Leu Asn Gly
 65                  70                  75                  80

Ser Asn Ile Glu Ile Ile Leu Asp Val Pro Asn Gln Asp Leu Glu Ala
                 85                  90                  95

Leu Ala Asn Ser Ser Ile Ala Asn Gly Trp Val Gln Asp Asn Ile Arg
             100                 105                 110

Ser His Phe Pro Tyr Val Lys Phe Lys Tyr Ile Ser Ile Gly Asn Glu
         115                 120                 125

Val Ser Pro Ser Asn Asn Gly Gln Tyr Ser Gln Phe Leu Leu His Ala
    130                 135                 140

Met Glu Asn Val Tyr Asn Ala Leu Ala Ala Ala Gly Leu Gln Asp Lys
145                 150                 155                 160

Ile Lys Val Thr Thr Ala Thr Tyr Ser Gly Leu Leu Ala Asn Thr Tyr
                165                 170                 175

Pro Pro Lys Asp Ser Ile Phe Arg Glu Glu Phe Lys Ser Phe Ile Asn
            180                 185                 190

Pro Ile Ile Glu Phe Leu Ala Arg Asn Asn Leu Pro Leu Leu Ala Asn
        195                 200                 205

Ile Tyr Pro Tyr Phe Gly His Ile Tyr Asn Thr Val Asp Val Pro Leu
    210                 215                 220

Ser Tyr Ala Leu Phe Asn Gln Gln Gly Thr Asn Ser Thr Gly Tyr Gln
225                 230                 235                 240

Asn Leu Phe Asp Ala Leu Leu Asp Ser Ile Tyr Phe Ala Val Glu Lys
                245                 250                 255

Ala Gly Gly Pro Asn Val Glu Ile Ile Val Ser Glu Ser Gly Trp Pro
            260                 265                 270

Ser Glu Gly Asn Ser Ala Ala Thr Ile Glu Asn Ala Gln Thr Tyr Tyr
        275                 280                 285

Arg Asn Leu Val Asn His Val Lys Gly Gly Ala Gly Thr Pro Lys Lys
    290                 295                 300

Pro Gly Arg Ile Val Glu Thr Tyr Leu Phe Ala Met Phe Asp Glu Asn
305                 310                 315                 320

Glu Lys Asn Gly Glu Val Thr Glu Lys His Phe Gly Leu Phe Tyr Pro
                325                 330                 335

Asn Arg Thr Ala Lys Tyr Gln Leu Asn Phe Met Tyr Ser
            340                 345
```

GENETICALLY MODIFIED PLANTS WITH ENHANCED RESISTANCE TO FUNGAL DISEASES AND A METHOD OF PRODUCTION THEREOF

This application is entitled to and claims priority benefit to U.S. provisional application Ser. No. 60/331,749, filed Nov. 20, 2001, which is incorporated herein by reference in its entirety.

1. FIELD OF THE INVENTION

The present invention relates to genetically modified plants, and in particular genetically modified potato plants. The genetically modified plants have an enhanced resistance to pathogens following transformation of the plant with a vector comprising a chitinase gene with two or more chitin-binding domains and a β-1,3-glucanase gene, and in particular, a Brassica chitinase gene with two chitin-binding domains and a Hevea β-1,3-glucanase gene. The invention further relates to a recombinant vector that transforms potato plants so as to confer upon the potato plants immunity against pathogens. The vector comprises a chitinase gene having two or more chitin-binding domains; and a β-1,3-glucanase gene. The invention further relates to a method of producing an enhanced pathogen resistance plant by expressing a chitinase gene and a β-1,3-glucanase gene.

2. BACKGROUND OF THE INVENTION

Plants play a critical role as nutrients for animals, including humans, and for the production of substances useful as pharmaceuticals, cosmetics and the like. The steady growth in the world's population results in increasing needs for plant crops. This increased need must be satisfied with reduced soil resources available to agriculture. Increased crop yield can be provided with existing soil resources by engineering plant species that grow better and that are more resistant to plant pathogens.

Plants are subjected to threats by numerous pathogens, e.g., fungi, bacteria, viruses, insects and nematodes. A small fraction of pathogens succeed in invading plant tissue and thereby cause disease. In particular, potato is a major food crop that is highly susceptible to fungal infection. One strategy to combat fungal disease include the use of chemical fungicides. However, this involves high expense and environmental cost. Previous attempts to increase pathogen resistance in plants include the expression of the tomato Mi-1.2 nematode resistance gene in a nematode-susceptible tomato line. The resulting transgenic tomato plants showed resistance to the root knot nematodes M. javanica strain VW4 and M. incognita strain VW6 in most of the transgenic plants but not against M. javanica strain VW5, thus resembling the specificity of the Mi gene in wild-type plants (Milligan et al., 1998, The Plant Cell 10:1307–1319).

In another study, plant resistance was induced by activating an inactive transgene encoding the Cf-9 resistance gene product through excision of a transposable element from that gene in a plant that expressed Avr9, a Cf-9 elicitor (WO 95/31564). Also, the plant Prf resistance gene was overexpressed in tomato plants, leading to enhanced resistance to P. s. pathovar tomato strain DC3000, X c. pv. vesicatoria strain 56, R. solanacearum strain 82 bacterial pathogens and TMV viral pathogen (Oldroyd et al., 1998, Proc. Natl. Acad. Sci. USA 95:10300–10305).

In another attempt to increase plant resistance, glucose oxidase was expressed in potato plants to generate $H_2O_2$, a reagent produced during plant defense responses, through glucose oxidation. $H_2O_2$ elevation in transgenic potato plants was shown to increase resistance to E. carotovora subspecies carotovora and P. infestans (Wu et al., 1995, The Plant Cell 7:1357–1368). Transgenic rice plants were generated expressing the potato proteinase inhibitor II gene, rendering the plants more resistant to pink stem borer larvae of Sesamia inferens (Duan et al., 1996, Nature Biotechnology 14:494–498). Also, resistance to G. pallida was enhanced in transgenic potato plants expressing cowpea trypsin inhibitor (U.S. Pat. No. 5,494,813). The expression of a protein that disrupts the feeding structure of plant nematode pathogens is suggested in U.S. Pat. No. 5,866,777 and the expression of lytic proteins in apple tree plants is discussed in U.S. Pat. No. 5,824,861.

Pathogenesis-related (PR) proteins including chitinases and β-1,3-glucanases are produced by plants in response to infection by pathogens. Chitinase hydrolyzes chitin, a major component of fungal cell walls while β-1,3-glucanase hydrolyzes the glucan component (Boller et al., 1985, In: J. L. Key et al. ed., Cellular and Molecular Biology of Plant Stress, Alan R. Liss, New York, pp. 247–262; Boller, 1992, In: S. J. Gurr et al. (ed), Molecular Plant Pathology Volume II, A Practical Approach, IRL press, Oxford, pp. 23–30). Schlumbaum et al. (1986, Nature 324:365–367) have demonstrated that purified plant chitinases demonstrate antifungal activity in vitro and the expression of chitinases with one chitin-binding domain in transgenic plants enhances their resistance against fungal pathogens (Broglie et al., 1991, Science 254:1194–1197; Lin et al., 1995, Bio/Technology 13:686–691). In a resistant cultivar of Brassica napus, the mRNA of ChB4, a chitinase with one chitin binding protein, was induced by Phoma lingam infection and was detected within a day on northern blot analysis (Rasmussen et al., 1992, Plant Mol. Biol. 20:277–287). Also, chitinases act synergistically with β-1,3-glucanases in inhibiting fungal growth (Mauch et al., 1988, Plant Physiol. 88:936–942; Zhu et al., 1994, Bio/Technology 12:807–812; Jach et al., 1995, Plant J. 8:97–109)

There remains a need for plants, such as potato plants, with enhanced resistance to fungus. In particular, potato plants with enhanced resistance to soil-borne fungus.

Citation of a reference in this or in any section of the specification shall not be construed as an admission that such reference is prior art to the invention.

3. SUMMARY OF THE INVENTION

The present invention is based upon the observation of the present inventors that transcription and translation of BjCHI1 that encodes a chitinase with a double-chitin binding domain are induced upon fungal infection. Chitinases and β-glucanases are hydrolytic enzymes acting on chitin and β-1,3-glucan, two major carbohydrates components of the fungal cell wall. The invention seeks to provide fungal protection in plants by transforming plants, such as crops, and specifically potato plants, with enzymes involved in the breakdown of the pathogen-related carbohydrate components and specifically fungal cell wall. In a specific embodiment, the invention provides transgenic potato plants with enhanced protection against Rhizoctania solani, a soil-borne fungus, by the co-expression of Brassica juncea chitinase with two chitin-binding domains and Hevea β-1, 3-glucanase.

The present invention provides transgenic plant having therein a gene comprising a promoter, operably associated with a coding sequence for chitinase comprising two or more chitin-binding domains, and a terminator. In specific embodiments, the chitinase comprises two, three, four or five chitin-binding domains respectively. Plant cells containing a gene comprising a nucleic acid sequence encoding chitinase are also an aspect of this invention, as are other plant parts, such as for example, seed of the transformed plant containing a gene according to the invention.

In a specific embodiment, the present invention provides transgenic potato plants having therein a gene comprising a promoter, operably associated with a coding sequence for *Brassica juncea* chitinase, and a terminator. Potato plant cells containing a gene comprising a nucleic acid sequence encoding *Brassica juncea* chitinase are also an aspect of this invention, as are other plant parts, such as for example, seed of the transformed plant containing a gene according to the invention.

In a specific embodiment, the present invention further provides transgenic potato plants having therein a gene comprising a promoter, operably associated with a coding sequence for β-1,3-glucanase, and a terminator. Potato plant cells containing a chimeric gene comprising a nucleic acid sequence encoding β-1,3-glucanase are also an aspect of this invention, as are other plant parts, such as for example, seed of the transformed plant containing a gene according to the invention.

In a specific embodiment, the present invention further provides transgenic potato plants having therein a gene comprising a promoter, operably associated with a coding sequence for Hevea β-1,3-glucanase, and a terminator. Potato plant cells containing a chimeric gene comprising a nucleic acid sequence encoding Hevea β-1,3-glucanase are also an aspect of this invention, as are other plant parts, such as for example, seed of the transformed plant containing a gene according to the invention.

In a specific embodiment, the present invention further provides transgenic plant comprising a chitinase and a β-1,3-glucanase. In a specific embodiment, the chitinase and the β-1,3-glucanase are encoded in separate vectors. In another specific embodiment, the chitinase and the β-1,3-glucanase are encoded in the same vector. In a specific embodiment, the chitinase has two or more chitin-binding domains. In another specific embodiment, the chitinase is BjCHI1 and the β-1,3-glucanase is HbGLU.

In a specific embodiment, the present invention further provides transgenic plant having therein a chimeric gene comprising a first promoter, operably associated with a coding sequence for *Brassica juncea* chitinase, and a terminator, a second promoter, operably associated with a coding sequence for Hevea β-1,3-glucanase, and a second terminator. In a specific embodiment, the genetically modified plants have an enhanced resistance against fungus following the introduction, by recombinant DNA techniques, of coding sequences for *Brassica juncea* chitinase and Hevea β-1,3-glucanase. In a specific embodiment, potato (*Solanum tuberosum* L. cv. Desiree) is transformed via Agrobacterium-mediated transformation using pBI121-derived plant transformation plasmid that carries both BjCHI1 and HbGLU cDNAs.

In another embodiment, additional gene sequences coding for plant defense proteins may be introduced into the plant in addition to the coding enzyme for chitinase and β-1,3-glucanase. Such gene sequences includes, but are not limited to, genes encoding ribosome-inactivating proteins, lectins and agglutinins. In a specific embodiment, serine proteinase inhibitor may be used. In another specific embodiment, SaPIN IIa (Xu Z. F. et al., 2001, Plant Molecular Biology 47:727–738) may be used.

In a specific embodiment, the present invention provides plant cells that comprise a chimeric gene. The chimeric gene comprises a nucleic acid sequence encoding a chitinase that comprises two or more chitin-binding domain and a nucleic acid sequence encoding a β-1,3-glucanase. In a specific embodiment, the chimeric gene comprises a nucleic acid sequence encoding a chitinase comprising four chitin-binding domains. In a specific embodiment, the plant cells are resistant to insect or bacteria or both. In a specific embodiment, the nucleic acid sequences encode *Brassica juncea* chitinase and Hevea β-1,3-glucanase.

In a specific embodiment, the present invention further provides a method of enhancing the resistance of plant to pathogens, the method comprising the steps of introducing into the plant genome a nucleic acid sequence encoding a chitinase that comprises two or more chitin-binding domain and regenerating a plant having an altered genome. In a specific embodiment, the chitinase is *Brassica juncea* chitinase under the direction of a suitable promoter and a suitable terminator.

In a specific embodiment, the present invention further provides a method of enhancing the resistance of plant to pathogens, the method comprising the steps of introducing into the plant genome a nucleic acid sequence encoding Hevea β-1,3-glucanase under the direction of a suitable promoter and a suitable terminator, and regenerating a plant having an altered genome. In a specific embodiment, the glucanase is Hevea β-1,3-glucanase under the direction of a suitable promoter and a suitable terminator.

In a specific embodiment, the present invention further provides a method of enhancing the resistance of plant to pathogens, the method comprising the steps of introducing into the plant genome a nucleic acid sequence encoding *Brassica juncea* chitinase under the direction of a suitable promoter and a suitable terminator, and Hevea β-1,3-glucanase under the direction of a suitable promoter and a suitable terminator, and regenerating a plant having an altered genome.

4. DESCRIPTION OF THE FIGURES

In order that the invention may be easily understood and readily carried into effect, reference will now be had, by way of example, to the following diagrammatic drawings in which:

FIG. 1 shows the nucleotide sequence of *B. juncea* BjCHI1 and structure of BjCHI1. A. Nucleotide sequence of BjCHI1 (SEQ ID NO:1) with deduced amino acid sequence (SEQ ID NO:2) shown under the nucleotide sequence. The chitin-binding domains are underlined. The hinge region is underlined with a dotted line. The putative polyadenylation signal is double underlined. The putative cleavage sites for the N-terminal signal peptide and the C-terminal vacuolar targeting peptide are marked (↓). The chitin-binding domains are tandem repeats that differ in two amino acids. The amino acid residues "S" at position 25 and "E" at position 30 of BjCHI1 in the first chitin-binding domain and in the second domain, amino acid residues "R" at position 76 and "A" at position 81. Positions of primers (P1 to P4) are boxed; for P2 and P4, these nucleotides correspond to their complementary sequences. HindIII restriction sites are shown. B. Schematic representation of BjCHI1. The N-terminal signal peptide (black box SP) precedes two chitin-binding domains (CBD1, amino acids 22–61; CBD2, amino acids 73–112) that are separated by a spacer (gray box S). CBD2 and the chitinase catalytic domain (amino acids 146–393) are linked by a hinge region (crossed box H). Vacuolar targeting sequence, hatched box v.

FIG. 2 is a comparison of BjCHI1 (SEQ ID NO: 2) with other classes of plant chitinases. A. Tobacco Chia1 (SEQ ID NO: 17)(Shinshi et al., 1990, Plant Mol. Biol. 14:357–368) and Chia2 (SEQ ID NO: 18) (Payne et al., 1990, Proc. Nail. Acad. USA 87:98–102), bean Chia4 (SEQ ID NO: 19) (Margis-Pinheiro et al., 1991, Plant Mol. Biol. 17:243–253), stinging nettle Chia5 (SEQ ID NO: 20) (Lerner and Raikhel, 1992, J. Biol. Chem. 287:11085–11091) and sugar beet Chia6 (SEQ ID NO: 21)(Berglund et al. 1995, Plant Mol. Biol. 27:211–216). Dotted gaps are used to optimize alignment. Asterisks denote positions of identity. The putative cleavage sites of the signal peptide and the vacuolar targeting sequence are marked (↓). The chitin-binding domains of BjCHI1 are underlined. The hinge region of BjCHI1 is underlined with a dotted line. The PPTP (residues 38–72 of SEQ ID NO: 2) repeats in the spacer and hinge are marked with arrows. The synthetic peptide (YKEEIDKSDPHC; SEQ ID NO:8), which corresponds to amino acid residues 231 to 242 of BjCHI1, that is used to raise polyclonal antibodies is boxed. The sequence NYNYG (SEQ ID NO: 9), which corresponds to amino acid residues 268 to 272 of BjCHI1, is boxed. The eight amino residues conserved in Chia classes are marked (♦). Identity (%) to BjCHI1 is shown at the end of the sequences with comparison within the chitinase catalytic domain In parenthesis. B. Schematic representation of BjCHI1, Chia1 end UDA1 showing positions of the cysteine residues (C) involved in formation of disulfide bridges (denoted by linked lines above the bar). Black box represents signal peptide (SP): gray box, spacer (S); crossed box, hinge region (H); and hatched box, vacuolar targeting sequence (V).

Figure 3:
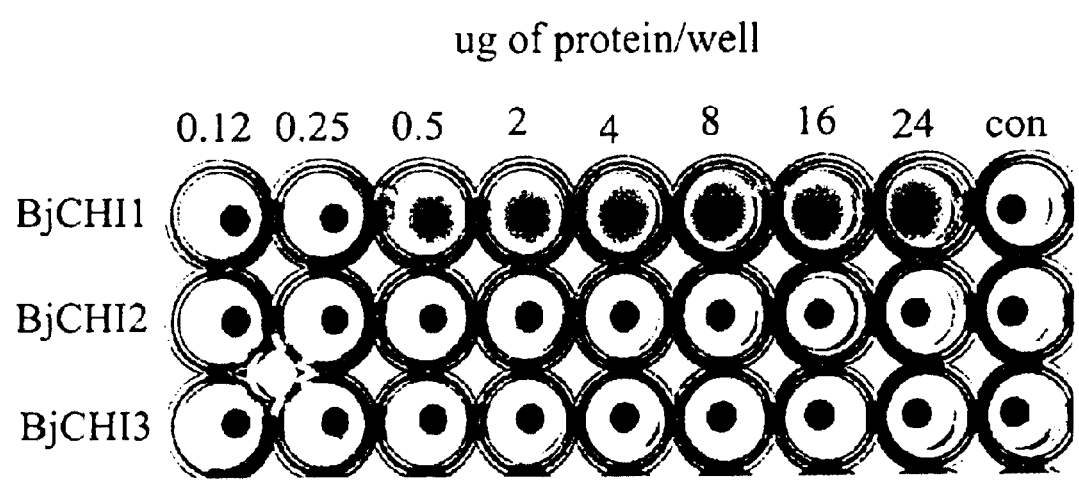

FIG. 3 shows the result of agglutination activity assays on BjCHI1, BjCHI2, and BjCHI3, BjCHI2 and BjCHI3 are BjCHI1 derivatives that contain one and no chitin-binding domain, respectively. Agglutination assays were performed with FPLC-purified Pichia-expressed chitinases according to Does et al. (1999, Plant Physiol. 120:421–431). Varying amounts (0.12, 0.25, 0.5, 2, 4, 8, 16 or 24 μg) of FPLC-purified proteins (BjCHI1, BjCHI2 and BjCHI3) from Pichia-expressing cultures were added to 30 microliters trypsin-treated rabbit erythrocytes in each well on a microtiter plate. Five times concentrated phosphate saline was added to a final volume of 60 μl in each well. In the control wells (i.e., "con"; last well of each row), phosphate buffered saline replaced the proteins.

FIG. 4 is an analysis of BjCHI1-related genes in the genome of B. juncea. A. Southern blot analysis. DNA digested with EcoRI (lane 1), HindII (lane 2), HindIII (lane 3) and XbaI (lane 4), hybridized to $^{32}$P-labelled BjCHI1 cDNA, washed in 0.1×SSC, 0.1% SDS at room temperature. Lanes 5 to 8 represent the same blot washed at 65° C. B. PCR products with primers, P1 and P2 (lane 1) or P2 and P3 (lane 2) electrophoresed in 2% agarose gel, stained with ethidium bromide. C. Southern blot of agarose gel shown in (b) hybridized to $^{32}$P-labelled BjCHI1 cDNA.

FIG. 5 shows the nucleotide sequence of Hevea β-1,3-glucenase. A. Nucleticle sequence of Hevea β-1,3-glucanase (SEQ ID NO:3). B. Deduced amino acid sequence of Hevea β-1,3-gluoanase (SEQ ID NO:4). C. Comparison of the deduced amino acid sequence of Hevea (Hb) β-1,3-glucanase (SEQ ID NO: 4) and that of N. plumbaginifolia (Np) gnl (SEQ ID NO: 22)(De Loose et al., 1988, Gene 70: 12–23), Class II (CII) (SEQ ID NO: 23). Class III (CIII) (SEQ ID NO: 24) and Class IV (CIV) (SEQ ID NO: 25) β-1,3-glucanase. Positions of identity are denoted by dots. The putative N-glycosylation sites in Hevea β-1,3-glucanase are marked with asterisks. The predicted N-terminal extension and C-terminal extension of Hevea β-1,3-glucanase are overlined and underlined, respectively.

Figure 6:
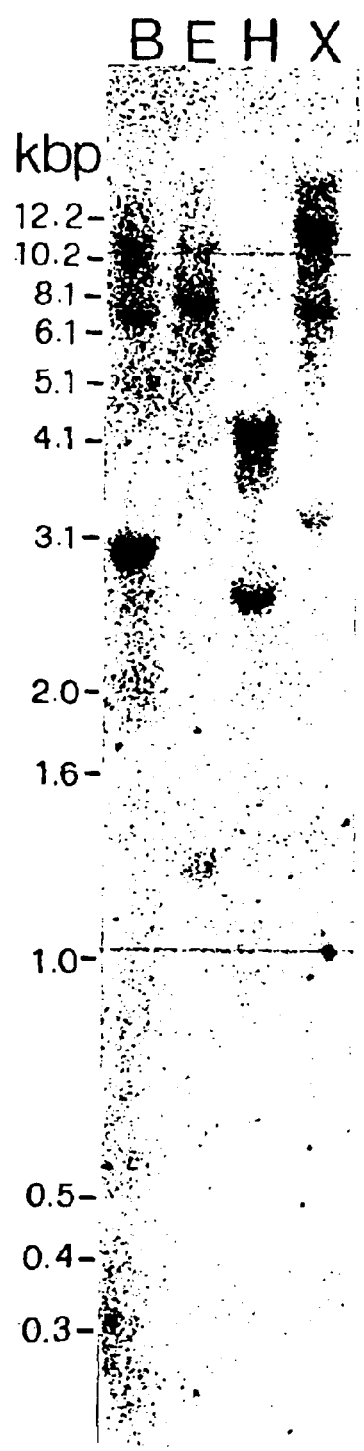

FIG. 6 shows genomic Southern analysis. Hevea genomic DNA (20 μg) was digested with BamHI (B), EcoRI (E), HindII (H) and XbaI (X), separated by gel electrophoresis, blotted onto Hybond N (Amersham) membrane and hybridized with $^{32}$P-labelled Hevea β-1,3-glucanase cDNA probe.

Figure 7:
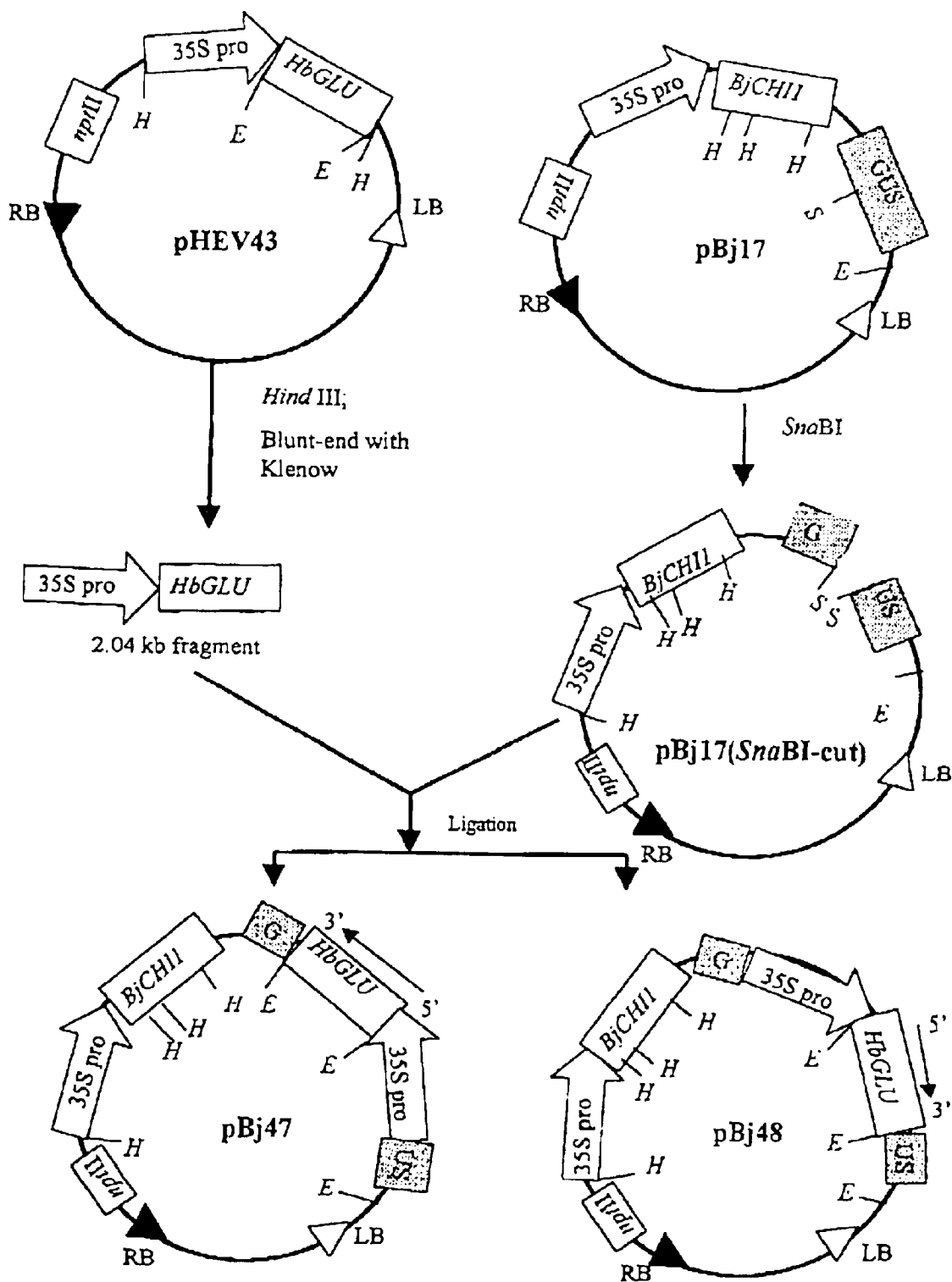

FIG. 7 shows the construction of plasmids pBj17, pHEV43 and pBj47 and pBj48. Plasmid pHEV43 was generated by cloning a 1.2 kb SmaI-HindII fragment of full-length HbGLU cDNA in the SmaI site of plasmid pBI121, downstream from the CaMV 35S promoter. Plasmid pBj17 was generated by cloning a 1.3 kb SmaI fragment of full-length BjCHI1 cDNA in the SmaI site of pBI121. The CaMV 35S promoter drives expression of the BjCHI1 cDNA in pBj17. Subsequently the blunt-end treated 2.04 kb HindIII fragment from pHEV43 was cloned into the SnaBI of pBj17. Since this blunt-ended fragment can insert in two possible orientations, plasmids pBj47 and pBj48 were obtained, each of which contains both the HbGLU cDNA and the BjCHI1 cDNA on a single plasmid. In pBj47, the chitinase and the glucanase cDNAs are each transcribed from the CaMV 35S promoter in opposite directions while in pBj48, these two DNAs are transcribed in the same direction. RB, right border of T-DNA; LB, left border of T-DNA; nptII, gene encoding neomycin phosphotransferase for kanamycin selection transcribed from the Nos promoter; 35S pro, CaMV 35S promoter; GUS; promoterless gene encoding β-glucuronidase; H. HindIII; E, EcoRI; S, SnaBI. The arrow above the HbGLU cDNA in the maps for plasmids pBj47 and pBj48 shows the direction of transcription of this cDNA from its 5'-end (5') to its 3'-end (3'). Drawings are not to scale.

FIG. 8 shows BjCHI1 expression is induced in B. juncea following R. solani infection: (a) Northern blot analysis using $^{32}$P-labelled BjCHI1 cDNA of total RNA from B. juncea leaves harvested 0 day (lane 1), 1 day (lane 2), 2 days (lane 3), 3 days (lane 4), 4 days (lane 5), 5 days (lane 6), 6 days (lane 7), 7 days (lane 8), 8 days (lane 9) and 9 days (lane 10) after growth in R. solani infected soil. The same blot reprobed with a $^{32}$P-labelled 18S rDNA probe is shown below. The arrow denotes the 1.3 kb BjCHI1 mRNA and the arrowhead, 18S rRNA; (b) Western blot analysis using anti-BjCHI1 antibodies. Total protein from B. juncea leaves were harvested 0 day (lane 1), 1 day (lane 2), 2 days (lane 3), 3 days (lane 4), 4 days (lane 5), 5 days (lane 6), 6 days (lane 7), 7 days (lane 8), 8 days (lane 9) and 9 days (lane 10) after growth in R. solani infected soil. The cross-reacting 37 kDa BjCHI1 band is denoted with an arrow. The faint band above this band is likely a precursor protein; (c) Coomassie-stained protein gel identically loaded as in (b) to demonstrate equal amounts of protein are loaded in each well.

FIG. 9 shows Northern blot analysis of $R_0$ transgenic potato plants: A. Expression of the 1.2 kb hybridizing HbGLU mRNA (denoted by arrowhead) as detected with a $^{32}$P-labelled HbGLU cDNA probe in untransformed potato (lane 1) and transgenic potato lines pBj47-$P_{10}$ (lane 2), pBj47-$P_8$ (lane 3), pBj47-$P_7$ (lane 4) and pHEV-$P_{14}$ (lane 5); B. Expression of the 1.3 kb BjCHI1 hybridizing mRNA (denoted by arrow) as detected with a $^{32}$P-labelled BjCHI1 cDNA probe in untransformed potato (lane 1) and transgenic potato lines pBj47-$P_{10}$ (lane 2), pBj47-$P_8$ (lane 3), pBj47-$P_7$ (lane 4), pBI121 transform potato (lane 5) and pBj17-$P_6$ (lane 6).

FIG. 10 shows Southern blot analysis of $R_0$ transgenic potato plants: A. Using a $^{32}$P-labelled HbGLU cDNA probe and EcoRI-digested DNA from untransformed potato (lane 1), pBI121 transformed potato (lane 2) and transgenic potato lines pHEV43-$P_{14}$ (lane 3), pBj47-$P_7$ (lane 4), pBj47-$P_8$ (lane 5) and pBj47-$P_{10}$ (lane 6). Arrowhead denotes 1.2 kb EcoRI-hybridizing band; B. Using a $^{32}$P-labelled BjCHI1 cDNA probe and HindIII-digested DNA from untransformed potato (lane 1), pBI121 transformed potato (lane 2) and transgenic potato lines pBj47-$P_7$ (lane 3), pBj47-$P_8$ (lane 4), pBj47-$P_{10}$ (lane 5) and pBj17-$P_6$ (lane 6). Arrow denotes 0.9 kb HindIII-hybridizing band; C. Using a $^{32}$P-labelled BjCHI1 cDNA probe and EcoRI-digested DNA from untransformed potato (lane 1), pBI121 transformed potato (lane 2) and transgenic potato lines pBj47-$P_{10}$ (lane 3), pBj47-$P_8$ (lane 4) and pBj47-$P_7$ (lane 5).

Figure 11A:
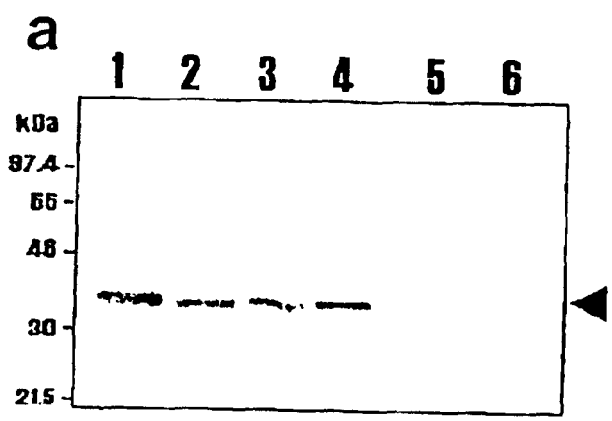

FIG. 11 shows Western blot analysis of $R_0$ transgenic potato plants: A. Western blot analysis using anti-HbGLU antibodies on crude protein from transgenic potato lines pBj47-$P_7$ (lane 1), pBj47-$P_8$ (lane 2), pBj47-$P_{10}$ (lane 3), pHEV43-$P_{14}$ (lane 4), pBI121 transformed potato (lane 5) and untransformed potato (lane 6). Band corresponding to HbGLU (35 kDa) is denoted by an arrowhead; B. Western blot analysis using anti-BjCHI1 antibodies on crude protein from transgenic potato lines pBj47-$P_7$ (lane 1), pBj47-$P_8$ (lane 2), pBj47-$P_{10}$ (lane 3), pHEV43-$P_{14}$ (lane 4), pBI121 transformed potato (lane 5), untransformed potato (lane 6) and transgenic potato line pBj17-$P_6$ (lane 7). Band corresponding to BjCHI1 (52 kDa) is denoted by an arrow.

FIG. 12 shows glucanase and chitinase assays on transgenic potato lines: A. Glucanase assays measured in optical density at 500 nm using crude protein from pBI121-transformant and transgenic $R_0$ lines transformed with pBj47; B. Chitinase assays measured in optical density at 550 nm using crude protein pBI121-transformant and transgenic $R_0$ lines transformed with pBj47. Error bars represent standard deviations of three separate experiments.

Figure 13B:
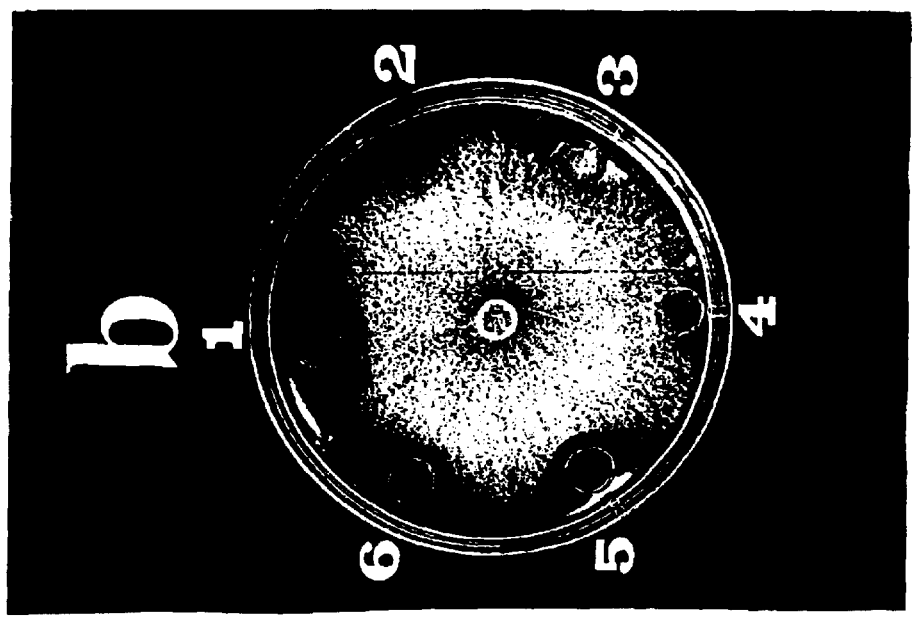
Figure 13A:
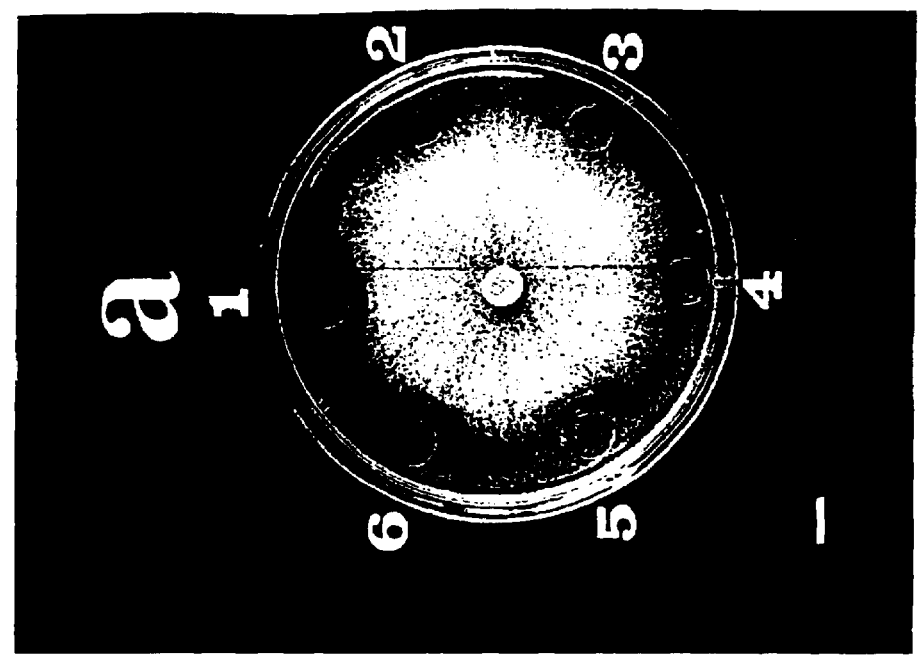
Figure 14A:
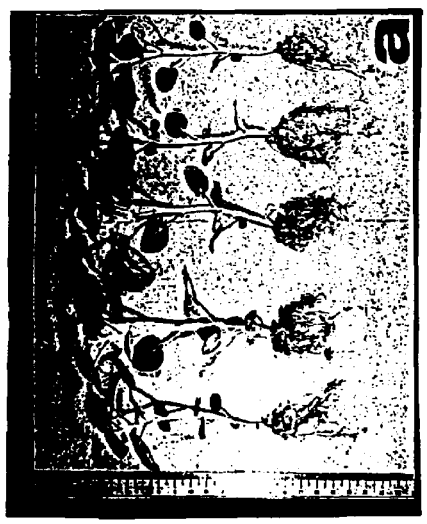
Figure 14B:
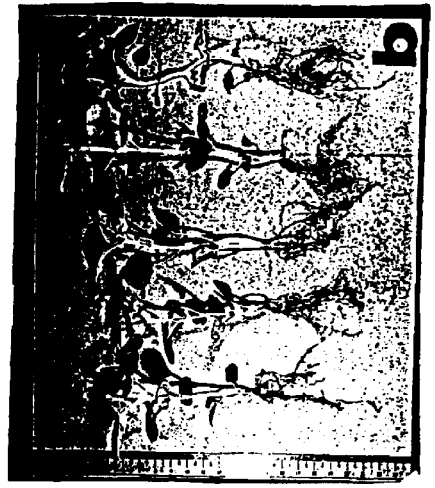
Figure 14C:
Figure 14D:
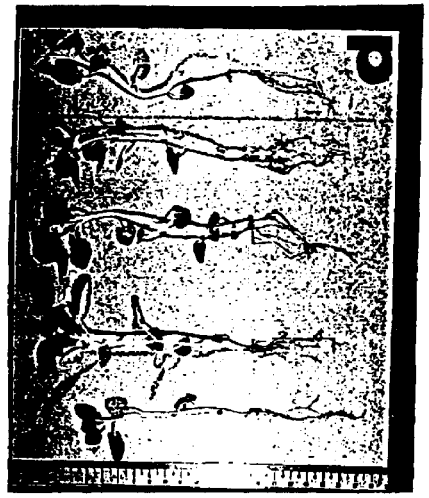

FIG. 13 shows In vitro hyphal inhibition assay using *T. viride*: A. Fungal growth 16 h after addition of 50 μg protein extract from each potato line in well. Well 1: transgenic potato line pBj47-$P_{10}$ co-expressing BjCHI1 and HbGLU; well 2: buffer-only control; well 3: wild-type potato Desiree; well 4: potato pBI121 transformant; well 5: transgenic potato line pBj17-$P_6$ expressing BjCHI1 and well 6: transgenic potato line pHEV43-$P_{14}$ expressing HbGLU; B. Fungal growth of plate shown in FIG. 13A, 24 h after addition of 50 μg protein extract. Bar at lower left represents 0.9 cm.

FIG. 14 shows In vivo fungal bioassays using *R. solani*. Potato plants were transferred to soil preinoculated with *R. solani*. The plants were examined and photographed after two weeks following transplantation: A. Transgenic potato line pBj47-$P_{10}$ co-expressing BjCHI1 and HbGLU; B. Transgenic potato line pBj17-$P_6$ expressing BjCHI1; C. Transgenic potato line pHEV43-$P_{14}$ expressing HbGLU; and D. Untransformed potato.

DETAILED DESCRIPTION OF THE INVENTION

Pathogen resistance is an important property in plants and a useful tool for the protection of plants, especially crop plants. The term "plant", as used herein, includes whole plants, plant parts, individual plant cells, groups of plants cells (e.g., cultured plant cells) and progeny thereof. The term "enhance" when used to describe an increase of resistance of a plant to a pathogen, as used herein, includes the increase of the resistance of a plant that may have no resistance, or some resistance or substantial resistance to the pathogen to effecting the increase in resistance.

Plant pathogens include, but are not limited to, bacteria, viruses, fungi, nematodes and insects. A pathogen may infect a plant and cause severe damage to that plant, including death. Upon infection, a plant may initiate a protective reaction to the pathogen, e.g., a hypersensitive response, depending on whether the plant can recognize the pathogen.

Pathogens of the various classes may change, for example, through mutagenesis. Also, new pathogens may arise that were not previously encountered by a plant species. For example, when a plant (e.g., a crop, a fruit, a vegetable, etc.) is introduced into a continent (for example, through importation), a plant species is likely exposed to pathogens it has not encountered before.

5.1 Cloning of a Polynucleotide Encoding *Brassica juncea* Chitinase and Hevea β-1,3-Glucanase Genes 5.1.1 Isolation of a *B. juncea* cDNA Encoding a Chitinase with Two Chitin-binding Domains When an amplified *B. juncea* cDNA library was screened for chitinase clones using a $^{32}$P-labeled Arabidopsis basic chitinase probe (Samac et al., 1990, Plant Physiol 93:907–914) prepared by PCR, five putative positives were obtained. Nucleotide sequence analysis showed that three clones had a 1.3 kb cDNA, designated BjCHI1, while the other two were incomplete-length cDNAs. BjCHI1 cDNA consists of 3 bp 5'-untranslated region, 1200 bp translated region, 86 bp 3'-untranslated region and a poly (A)+ tail (FIG. 1a). An open reading frame of 400 amino acids encodes a protein of predicted $M_r$ 42,774 (isoelectric point 4.7) with homology to plant Chia1 chitinases. Interestingly, this cDNA contains two 120 bp-repeats (nucleotides 67–186 and 220–339, FIG. 1a), which encode two chitin-binding domains linked by a 11-amino acid spacer; they differ in seven nucleotides resulting in two amino acid changes. A thirty-three amino acid hinge links the second chitin-binding domain to the chitinase catalytic domain (FIG. 1b). All other previously characterized chitinases contain only one chitin-binding domain. The chitin-binding domain is essential for chitin binding (Iseli et al., 1993, Plant Physiol. 103:221–226) and at least two such domains are required for cell agglutination (Peumans et al., 1995, Plant Physiol. 109:347–352). Occurrences of the chitin-binding domain are not limited to chitinases. This domain is also present in plant lectins, e.g. hevein, a 4.7 kDa protein from rubber latex (Van Parijs et al., 1991, Planta 183:258–264) has one chitin-binding domain. BjCHI1 is a unique chitinase with two chitin-binding domains and the present inventions have shown that these two chitin binding domains confer agglutination properties using Pichia-expressed BjCHI1 (see Section 5.1.2, infra). A chitinase with agglutination properties has not been previously reported.

5.1.2 Comparison of BjCHI1 with other Chitinases

FIG. 2A shows the alignment of BjCHI1 with representatives of different chitinase classes: Chia1 from *Nicotiana tabacum* (Shinshi et al., 1990, Plant Mol Biol 14:357–368), Chia2 from *N. tabacum* (Payne et al., 1990, Proc Natl Acad Sci USA 87:98–102), Chia4 from *P. vulgaris* (Margis-Pinheiro et al., 1991, Plant Mol Biol 17:243–253), Chia5 from *U. dioica* (Lerner et al., 1992, J Biol Chem 267:11085–11091) and Chia6 from *B. vulgaris* (Berglund et al., 1995, Plant Mol Biol 27:211–216). The representatives of Chia1 and Chia2 chitinases are those from *N. tabacum* that show highest identity to BjCHI1. Analysis of eighty-six plant chitinases has shown that eight amino acids are conserved within the Chia classes (Levorson et al., 1997, Plant Mol Biol Reptr 15:122–133). Seven of these are conserved in BjCHI1 (E-201, A-203, T-213, C-230, N-270, P-286 and G-377, FIG. 2A). The eighth residue (Q) is substituted by M-264 in BjCHI1 (FIG. 2A). Although BjCHI1 shares high identity to *N. tabacum* Chia1 (62.0%) and Chia2 (54.8%), it has two chitin-binding domains whereas Chia1 has one chitin-binding domain and Chia2 lacks this domain.

When compared with Chia1 chitinases from other plants, BjCHI1 shares 72.7% identity to *B. napus* (Hamel et al., 1993, Plant Physiol 101:1403), 70.2% identity to *A. thaliana* (Samac et al., 1990, Plant Physiol 93:907–914), 60.9% identity to *P. vulgaris* (Broglie et al., 1986, Proc Natl Acad Sci USA 83:6820–6824) and 5 1.8% identity to *Oryza sativa* (Zhu et al., 1994, BioTechnology 12:807–812). BjCHI1 also contains the sequence "NYNYG" (SEQ ID NO:9, amino acids 268 to 272, FIG. 2) highly-conserved in Chia1 chitinases (Verburg et al., 1992, J Biol Chem 267:3886–3893). Investigations on the catalytic site of a *Zea mays* chitinase have shown that modification of the first Y in this sequence "NYNYG" with 1-ethyl-3-(3-dimethylaminopropyl) carbodiimide resulted in loss of activity (Verburg et al., 1992).

Figure 2B:
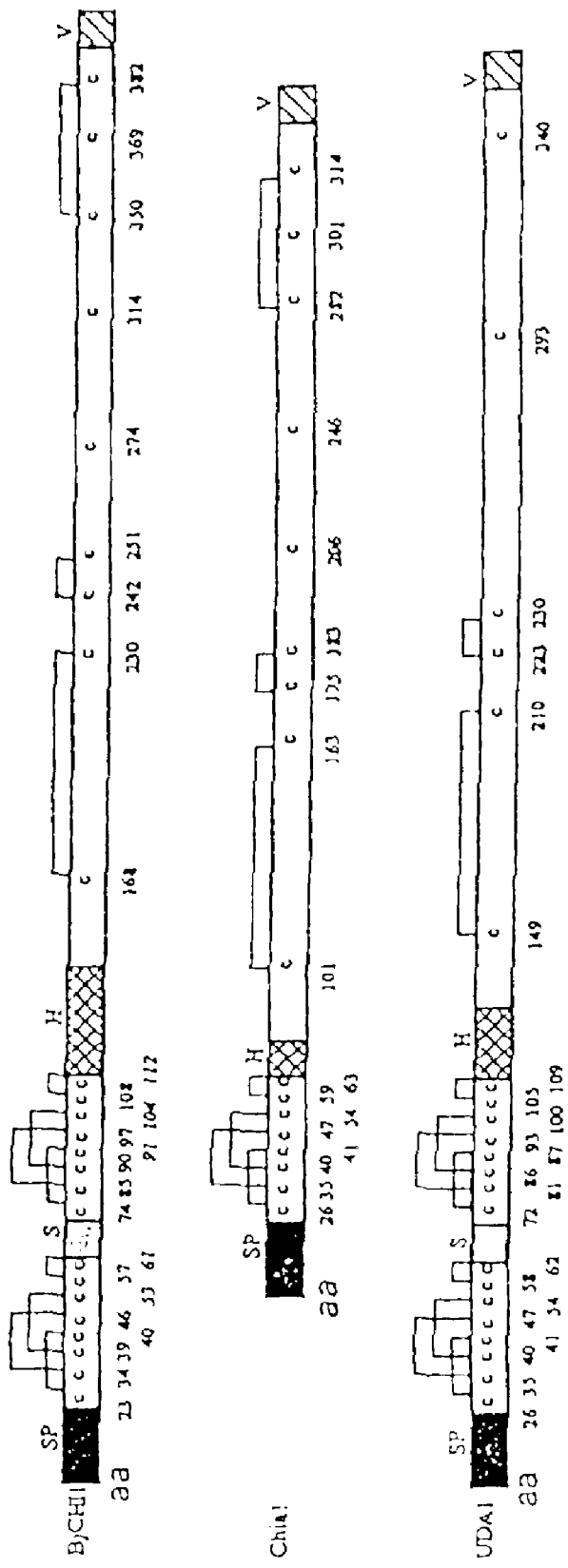

The presence of two chitin-binding domains would identify BjCHI1 with Chia5, of which only one example, *Urtica dioica* agglutinin, UDA1, is known (Levorson et al., 1997). UDA1 is a 372-amino acid precursor of stinging nettle (*U. dioica*) agglutinin (Lerner and Raikhel, 1992, J Biol Chem 267:11085–11091) and shows insect antinutrient activity (Chrispeels et al., 1991, Plant Cell 3:1–9). This precursor consists of a signal peptide, two chitin-binding domains and a chitinase catalytic domain. The 8.5 kD mature lectin consists of only 86-amino acids with two chitin-binding domains since the chitinase domain is cleaved-off post-translationally (Lerner and Raikhel, 1992). Although BjCHI1 and UDA1 have structural similarities they share only 36.9% identity (FIG. 2A). Comparison of disulfide bridges in chitinases, according to Beinterna (Beinterna, 1994, FEBS Letters 350:159–163), shows similarities between BjCHI1, Chia1 and UDA1 (FIG. 2B); the C-terminal disulfide bridge of Chia1, absent in UDA1, is present in BjCHI1. Unlike UDA1, the hinge and the spacer of BjCHI1 are proline-rich, with 63.6% and 54.5% proline residues, respectively. The sole member of Chia6 chitinase (Levorson et al., 1997), *B. vulgaris* Ch1, contains a hinge domain of 128 residues with 70.3% proline (Berglund et al., 1995, Plant Mol Biol 27:211–216). BjCHI1 and Ch1 both contain "PPTP" repeats (FIG. 2A). In contrast, Ch1 has only half a chitin-binding domain and there is only 45.2% identity between them.

The presence of the two-chitin binding domains in BjCHI1 prompted the present inventors to explore the BjCHI1's possibility of having agglutination properties. Accordingly, agglutination assays were performed with FPLC-purified Pichia-expressed BjCHJI1 according to Does et al. (1999, Plant Physiol. 120:421–431). As controls, BjCHI2 and BjCHI3 containing one and no chitin-binding domain, respectively, were employed. Briefly, BjCHI1, BjCHI2 and BjCHI3 were expressed in *Pichia pastoris* using yeast expression vector pPIC9K (Invitrogen). BjCHI1, BjCHI2 and BjCHI3 were cloned in-frame to the secretory signal peptide on pPIC9K, so that the fusion proteins would be secreted in the growth media. BjCHI1 contains both chitin-binding domains within amino acid residues 18 to 393 of the native protein (Zhao and Chye, 1999, Plant Mol. Biol. 40:1009–1018), fused to the secretory signal peptide on pPIC9K; BjCHI2 contains only one chitin-binding domain while BjCHI3 lacks both chitin-binding domains. BjCHI1, BjCHI2 and BjCHI3 DNAs were cloned into the EcoRI and NotI sites on vector pPIC9K. To this end the following primers were used in PCR: C1(forward) primer 5' CTGAAT-TCTCCTCC GGTGAGCAATGCG 3' (SEQ ID NO:5); C21 (forward) primer 5' CTGAATTCGGGGATC TTTCTG-GCATC 3' (SEQ ID NO:6); and C2(reverse) primer 5' GCGACTGCGGCCGCGT TACTACCTTCATTAAACG 3' (SEQ ID NO:7). The forward primers were designed with one EcoRI site and the reverse with one NotI site. The 1.1 kb DNA encoding BjCHI1 was amplified by PCR with C1 and C2 primers and pBj17 as template in PCR. The 0.95 kb DNA fragment encoding BjCHI2 (with one chitin-binding domain) was amplified by PCR with C1 and C2 primers and pBj28 as template. Plasmid pBj28 has been previously described in Fung et al. (2002, Plant Molecular Biology 50: 283–294). The 0.74 kb DNA encoding BjCHI3 (that lacks both two chitin-binding domains) was obtained by PCR using C21 and C2 primers and pBj17 as template. The PCR-amplified fragments were digested with EcoRI and NotI and cloned in the EcoRI and NotI sites of pPIC9K. The inserts in pPIC9K were analyzed by DNA sequence analysis before use in yeast transformation. The Pichia-expressed proteins were secreted in the growth media and precipitated using 65% ammonium sulfate according to the instructions provided by Invitrogen. Subsequently the crude extracts were purified by FPLC and the FPLC-purified proteins checked by western blot analysis with antibodies against BjCHI1 before use in agglutination assays. Since the peptide used in the preparation of polyclonal antibodies against BjCHI1 are retained within the BjCHI2 and BjCHI3 peptides, these BjCHI1 derivatives cross-reacted to these antibodies.

In agglutination assays, varying amounts (0.12, 0.25, 0.5, 2, 4, 8, 16 or 24 μg) of FPLC-purified proteins (BjCHI1, BjCHI2 and BjCHI3) from Pichia-expressing cultures were added to 30 μl trypsin-treated rabbit erythrocytes in each well on a microtiter plate (see FIG. 3). Five times concentrated phosphate saline was added to a final volume of 60 μl in each well. In the control wells, phosphate buffered saline replaced the proteins.

The results suggest that BjCHI1, by its agglutination properties, resembles insecticidal proteins that contain at least two chitin-binding domains including wheat germ agglutinin, *Urtica dioica* agglutinin, and lectins from tomato, rice and Datura (Chrispeels et al., 1991, supra). Since it has been suggested that plant lectins with two or more chitin-binding domains agglutinate cells by binding to glycoconjugates on bacterial and fungal surfaces and on the exoskeleton and intestinal lumen of herbivorous insects (Peumans et al., 1995, supra), the anti-microbial and anti-insect effects of BjCHI1 appear promising and warrant further investigations.

5.1.3 Genomic Organization of BjCHI1 in *B. juncea*

Southern blot analysis was used to investigate the presence of BjCHI1-related genes in *B. juncea*. Genomic DNA digested with EcoRI, HindII, HindIII and XbaI was hybridized to BjCHI1 cDNA. Only HindIII cleaves within the cDNA (FIG. 1A). Detection of six to nine hybridizing bands (FIG. 4A, lanes 1–4) indicates related genes in heterotetraploid *B. juncea*, a hybrid of *B. nigra* and *B. campestris*; bands could be due to genes encoding chitinases or proteins with chitin-binding domain(s). Further washing of the blot at 65° C. revealed fewer bands; bands in lanes 6–8 (FIG. 4A), are likely BjCHI1-specific. To investigate the occurrence of chitinases with one chitin-binding domain, PCR analysis was carried out using strategically-positioned primers. Primer P1 is adjacent to the region encoding the first chitin-binding domain while P2 is in the region encoding the chitinase domain that shows homology to other chitinases (FIG. 1A, FIG. 2). PCR amplification of BjCHI1 with these primers should give a 0.5 kb product, if no introns are between them; the first intron of the Arabidopsis chitinase gene (Samac et al., 1990) is located at a corresponding region after P2. The expected 0.5 kb product on agarose gel electrophoresis (FIG. 4B) hybridized to the BjCHI1 cDNA on Southern blot analysis, together with a weaker 0.35 kb band (FIG. 4C). This smaller band suggests the presence of a related chitinase with one chitin-binding domain and is weaker due to the specificity of the primers to BjCHI1. In contrast, PCR amplification of BjCHI1 with primers P2 and P3, shows a single band of 0.35 kb (FIGS. 4B and C, lane 2). P3, located in the region encoding the spacer (FIG. 1A), is BjCHI1-specific and was deemed suitable for measuring BjCHI1-specific mRNA expression in RT-PCR.

5.1.4 Isolation of a Hevea β-1,3-glucanase Gene

N. plumbaginifolia cDNA encoding β-1,3-glucanase, gnl cDNA (De Loose et al., 1988, Gene 70:12–23) was used as a heterologous hybridization probe to isolate the corresponding cDNA clones from Hevea. A cDNA library prepared from Hevea latex was screened by in situ plaque hybridization at 42° C. in a solution containing 30% formamide. Several putative Hevea cDNA clones encoding β-1,3-glucanase were isolated. Nucleotide sequence analysis carried out on two of the longest clones of 1.2 and 1.1 kb showed that they belonged to the same class. The full-length 1.2 kb cDNA consists of a 40 bp 5'-untranslated region, a 1125 bp coding region, a 76 bp 3'-untranslated region and a poly(A) tail. The coding region encodes a 374 amino acid basic protein with a predicted $M_r$ 41,305.

The nucleotide sequence of Hevea β-1,3-glucanase shows 68% nucleotide sequence identity to that of the N. plumbaginifolia gnl cDNA. Comparison of the predicted amino acid sequence of Hevea β-1,3-glucanase with that of the Class I β-1,3-glucanase encoded by gnl shows 66% amino acid homology (FIG. 5C). Hevea β-1,3-glucanase has 54%, 60% and 51% amino acid identity to Class II (N. tabacum PR-N (Linthorst et al., 1990, Proc Natl Acad Sci USA 87:8756–8760)), Class III (N. tabacum ec321391(Payne et al., 1990, Plant Mol Biol 15:797–808) and Class IV (N. tabacum sp41a (Ori et al., EMBO J, 1990, 9:3429–3436)) β-1,3-glucanase, respectively (FIG. 5C).

5.1.5 Hevea β-1,3-glucanase

Class I β-1,3-glucanase are synthesized as preproteins and the N-terminal extension and C-terminal extension are cleaved during or after transport of the protein to the vacuole (Shinshi et al., 1988, Proc Natl Acad Sci USA 85:5541–5545). The presence of an N-terminal extension (amino acid residues 1 to 36) and a C-terminal extension (amino acid residues 353 to 374) on the deduced amino acid sequence of Hevea β-1,3-glucanase further suggests that it belongs to Class I β-1,3-glucanase (FIG. 5C). The N-terminal extension of Hevea β-1,3-glucanase consists of a region (amino acid residues 4 to 19) enriched in serine and threonine residues, followed by a hydrophobic region (amino acid residues 22 to 29) (FIG. 5C). Although there is no significant amino acid sequence homology between the N-terminal of Hevea β-1,3-glucanase and gnl-encoded β-1, 3-glucanase, they both consist of a hydrophobic region typical of signal peptides (Von Heijne et al., 1985, J. Mol. Biol. 184:99–105) and is believed to be involved in protein targeting to the vacuole. Interestingly the N-terminal sequence of the propeptide of barley aleurain which has been shown be responsible for directing the protein to the vacuole is also rich in serine residue (Holwerda et al., 1992, Plant Cell 4:307–318). Comparison of the C-terminal extension of Hevea with that of N. plumbaginifolia shows that there is some conservation in amino acid sequence and in the putative N-glycosylation site (amino acid 364 in Hevea β-1,3-glucanase). The C-terminal extension, particularly amino acid residues 365 to 370 in Hevea, is rich in hydrophobic amino acids. It has been suggested that a hydrophobic/acidic motif structure, rather than the specific amino acid sequence forms a sorting signal in carboxy-extension propeptides (Nakamura et al., 1993, Plant Physiol 101:1–5). It has been established that the C-terminal extension and N-glycan of Class I isoforms of β-1,3-glucanase are removed during processing (Shinshi et al., 1988).

5.1.6 Genomic Organization of Hevea β-1,3-glucanase

The laticifer-specific cDNA which the present inventors had isolated was used in genomic Southern blot analysis to investigate the presence of a β-1,3-glucanase gene family in Hevea. Genomic DNA was obtained from young leaves following the procedure of Dellaporta et al., 1983, Plant Mol Biol Rep 1: 19–21. Total genomic DNA was restricted with BamHI, EcoRI, HindII and XbaI, electrophoresed and blotted. Southern blot analysis using the 1.2 kb Hevea β-1,3-glucanase probe showed that there were 2–4 hybridizing bands with each digest (FIG. 6). These results suggest that a low-copy gene family of β-1,3-glucanase is present in Hevea.

Other chitinases and β-1,3-glucanases may be isolated and characterized using techniques known in the art. A cDNA or genomic DNA specific for Brassica juncea chitinase and Hevea β-1,3-glucanase protein or nucleic acid may be cloned and sequenced in a variety of ways, e.g., dideoxy chain termination sequencing, see, e.g., Sambrook et al., supra.

The polynucleotides that may be used in the present invention include polynucleotides having the DNA sequences presented herein, and additionally include any nucleotide sequence encoding a contiguous and functional chitinase and β-1,3-glucanase encoding open reading frame (ORF) that hybridizes to a complement of the DNA sequences presented herein under highly stringent conditions. By way of example and not limitation, high stringency hybridization conditions can be defined as follows: The filter-bound DNA were hybridized in a solution containing 50% deionized formamide, 6×SSC, 5× Denhardt's, 1% SDS, 100 μg/ml denatured salmon sperm DNA at 42° C. overnight (about 4–16 hours), and washing in 0.1×SSC, 0.1% SDS at 65° C. (Ausubel F. M. et al., eds., 1989, Current Protocols in Molecular Biology, Vol. 1, Green Publishing Associates, Inc., and John Wiley & Sons, Inc., New York) and encodes a functionally equivalent gene product.

For oligonucleotide probes, by way of example and not limitation, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos).

Additionally contemplated polynucleotides that may be used in the present invention include any nucleotide sequences that hybridize under moderately stringent conditions to the complement of the DNA sequences that encodes a chitinase or β-1,3-glucanase. By way of example but not limitation, such moderately stringent conditions may include, e.g., washing in 0.2×SSC/0.1% SDS at 42° C. (Ausubel et al., 1989, supra).

Additionally contemplated polynucleotides that may be used in the present invention include any nucleotide sequences that hybridize under low stringency conditions to the complement of the DNA sequences that encode a chitinase or β-1,3-glucanase. By way of example and not limitation, procedures using such conditions of low stringency are described in Shilo and Weinberg, 1981, Proc. Natl. Acad. Sci. USA 78:6789–6792.

Moreover, a variant of chitinase and β-1,3-glucanase can also be used in the present invention. A variant may comprise one or more changes in the amino acid sequence of the enzyme, e.g., by way of addition, substitution, or deletion of one or more amino acids, compared with the wild type enzyme. Any change should not abolish the ability of the enzyme to perform its function, though it may increase or decrease this ability depending on the nature of the changes. Preferably, the amino acid changes are conservative.

In various embodiments, the chitinase and β-1,3-glucanase, fragment, variant, analog, or derivative may be expressed as a fusion, or chimeric protein product (comprising the enzyme, fragment, analog, or derivative joined via a peptide bond to a heterologous protein sequence (of a different protein)). Such a chimeric gene product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Preferably, the fragment, analog, and derivative of the enzyme in the fusion protein retains the ability to perform the enzyme's function.

A cDNA or genomic DNA specific for a plant chitinase and β-1,3-glucanase may be cloned through screening a cDNA or genomic DNA library. Such a library may be prepared, for example, from messenger RNA or genomic DNA from the plant. For general background on molecular biology techniques and on how to prepare a cDNA library and a genomic library, see, e.g., Ausubel F. M. et al., supra; Sambrook et al., 1989, supra; and U.S. Pat. No. 5,650,148.

The library may be screened with a nucleotide fragment specific for a part of the *Brassica juncea* chitinase and *Hevea* β-1,3-glucanase. For example, the protein sequence of a chitinase and β-1,3-glucanase may be determined using techniques well known to those of skill in the art, such as via the Edman degradation technique. (See, e.g., Creighton, 1983, "Proteins: Structures and Molecular Principles", W. H. Freeman & Co., New York, pp. 34–49). The amino acid sequence obtained may be used as a guide for the generation of oligonucleotide mixtures that can be used to screen a cDNA library for the cDNA sequence encoding the chitinase and β-1,3-glucanase.

Or, for example, two stretches of protein sequences specific for the chitinase and β-1,3-glucanase may be determined. A set of degenerate oligonucleotides specific for each stretch is prepared and the oligonucleotides are used in a polymerase chain reaction ("PCR") amplification. Oligonucleotides are at least about 6 nucleotides long, more preferably at least about 10, more preferably at least about 15, more preferably at least about 20, more preferably at least about 30, more preferably at least about 40 nucleotides. The template in the PCR reaction would be, for example, a mixture of cDNA or genomic DNA that is known to contain or suspected to contain a DNA polynucleotide specific for the chitinase and β-1,3-glucanase of interest. A cDNA template may be obtained in a variety of ways, for example, by isolating a mixture of different cDNA species from a cDNA library or, for example, by reverse transcribing total mRNA from a cell or organism known to (or suspected to) express the chitinase and β-1,3-glucanase. For background on PCR, see, e.g., Ausubel, supra, and PCR Protocols: A Guide to Methods and Applications, 1990, Innis, M. et al., eds. Academic Press, Inc., New York.

In order to clone a full length cDNA or genomic DNA sequence from any species or to clone variant or heterologous forms of the chitinase and β-1,3-glucanase, labeled DNA probes made from nucleic acid fragments corresponding to any of the polynucleotides discussed herein or made using the methods of the invention may be used to screen a cDNA library or a genomic DNA library (for example, a phage library) as described in, e.g., Ausubel F. M. et al., supra; Sambrook et al., 1989, supra.

5.2 Production of Antibodies

For the production of antibodies, various host animals may be immunized by injection with the chitinase and β-1,3-glucanase (e.g., one corresponding to functional domain of the chitinase and β-1,3-glucanase), truncated chitinase and β-1,3-glucanase polypeptides (a chitinase or β-1,3-glucanase in which one or more domains have been deleted), functional equivalents of the chitinase and β-1,3-glucanase, mutants of the chitinase and β-1,3-glucanase, or short peptides (or fragments) of chitinase and β-1,3-glucanase. Such host animals may include but are not limited to rabbits, mice, goats, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Antibodies useful for the present invention include monoclonal antibodies (see, e.g., Kohler et al., 1975, Nature 256:495–497; and U.S. Pat. No. 4,376,110), chimeric antibodies (see, e.g., Morrison et al., 1984, Proc. Natl. Acad. Sci., 81:6851–6855; Neuberger et al., 1984, Nature, 312:604–608; Takeda et al., 1985, Nature, 314:452–454), single chain antibodies (see, e.g., U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546), antibody fragments (see, e.g., Huse et al., 1989, Science, 246:1275–1281), anti-idiotypic antibodies or Fab fragments of such anti-idiotypes (see, e.g., Greenspan & Bona, 1993, FASEB J 7(5):437–444; and Nissinoff, 1991, J. Immunol. 147(8):2429–2438).

5.3 Expression of Chitinase and β-1,3-glucanase Using Recombinant DNA Technology Chitinase and β-1,3-glucanase, fragments thereof or fusion proteins thereof, are advantageously produced by recombinant DNA technology using techniques well known in the art. Such methods can be used to construct chimeric gene or expression vectors containing a chitinase or β-1,3-glucanase nucleotide sequence and appropriate transcriptional and translational control signals. These methods include, for example, in vitro recombinant DNA techniques, synthetic techniques, and in vivo genetic recombination. See, for example, the techniques described in Sambrook et al., 1989, supra, and Ausubel et al., 1989, supra. As used herein, the term chimeric gene refers to a combination of nucleic acid sequences for each part of the chimeric gene, which sequences have been engineered into relationship by recombinant DNA techniques, which sequences may also be in their separate parts endogenous or exogenous to the plant into which the chimeric gene is to be introduced.

Alternatively, RNA corresponding to all or a portion of a transcript encoded by a chitinase or β-1,3-glucanase nucleotide sequence may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

Any of host-expression vector system known in the art of biotechnology may be utilized to express the chitinase or β-1,3-glucanase nucleotide sequence including, but not limited to, expression in bacteria, yeast, insect cells, mammalian cells, eukaryotic cells and plant cells. In these expression systems, any selection system may be used. Such selection may comprise growth on a selective medium (e.g., antibiotics, minimal media, etc.) or the use of an indicator (e.g., a dye, a fluorescent reagent, etc.).

In cases where plant expression vectors are used, the expression of the chitinase and β-1,3-glucanase coding sequence may be driven by any of a number of regulatory elements. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, biolistics/particle bombardment, microinjection, electroporation, etc. For reviews of such techniques see, for example, Weissbach & Weissbach, 1988, Methods for Plant Molecular Biology, Academic Press, New York, Section VIII, pp. 421–463; and Grierson & Corey, 1988, Plant Molecular Biology, 2d Ed., Blackie, London, Ch. 7–9. As used herein, regulatory elements include but are not limited to inducible and non-inducible promoters, enhancers, operators and other elements known to those skilled in the art that drive and regulate expression.

Preferably the promoter is capable of directing expression in a particular tissue of the plant and/or at particular stages of development of the plant. The promoter may be heterologous or homologous to the plant. Preferably the promoter directs expression to the endosperm of the plant seed or to the roots or tuber of the plant. A preferred promoter is the high molecular weight glutenin (HMWG) gene of wheat. Other suitable promoters will be known to the skilled man, such as the promoters of gliadin, branching enzyme, ADPG pyrophosphorylase, starch synthase and actin, for example.

5.4 Transgenic Plants Expressing Chitinase and β-1,3-Glucanase

A transgenic plant with the ability to express a plant chitinase or β-1,3-glucanase polypeptide may be engineered by transforming a plant cell with a gene construct comprising a sequence encoding a plant chitinase and β-1,3-glucanase protein or polypeptide. In one embodiment, a plant promoter is operably associated with a sequence encoding the desired plant chitinase or β-1,3-glucanase protein or polypeptide. As used herein, the term "Operably associated" or "operably linked" refers to an association in which the regulatory regions (e.g., promoter, enhancer) and the nucleic acid sequence to be expressed are covalently joined and positioned in such a way as to permit transcription, and under the appropriate condition, translation. In a preferred embodiment of the present invention, the associated promoter is a strong and non tissue- or developmental-specific plant promoter (e.g., a promoter that strongly expresses in many or all plant tissue types). Examples of such strong, "constitutive" promoters include, but are not limited to, the CaMV 35S promoter (Odell et al., 1985, Nature 313:810–812), the T-DNA mannopine synthetase promoter, and their various derivatives. In another preferred embodiment, an inducible or repressible promoter is used to express the chitinase and/or β-1,3-glucanase of interest in a plant, for example, a tet operator promoter as described in Weinmann et al., 1994, The Plant Journal 5:559–569; or a glucocorticoid-inducible promoter as described in McNellis et al., 1998, The Plant Journal 14:247–257; or an ethanol inducible promoter as described in Caddick et al., 1998, Nature Biotechnology 16:177–180. See, also, Gatz, 1995, Methods In Cell Biology 50:411–424, which describes inducible and repressible gene expression systems for plants.

In one embodiment of the invention, a chitinase and/or β-1,3-glucanase is expressed in a plant so that the chitinase and/or β-1,3-glucanase polypeptide will be localized in the apoplastic space. The chitinase and/or β-1,3-glucanase may be directed to the apoplastic space, when expressed in a plant, by expressing the chitinase and/or β-1,3-glucanase polypeptide as a fusion protein together with a peptide that acts as a signal or transporter so that chitinase and/or β-1,3-glucanase is localized in the apoplastic space of the transgenic plant. A variety of signal or transporter peptides can be used, for example, the PR1b signal sequence as described in Lund et al., 1992, Plant Molecular Biology 18:47–53; or the PR-1a, b and c signal sequences as described in Pfitzner et al., 1987, Nucleic Acids Research 15:4449–4465. A fusion protein comprising a signal or transporter peptide and a chitinase and/or β-1,3-glucanase polypeptide may be constructed by linking polynucleotides specific for each component to each other (e.g., the polynucleotides are linked in frame) so that the desired fusion protein is made when the fusion polynucleotide is expressed in a transgenic plant. A skilled artisan would know how to construct a polynucleotide useful for expressing a chitinase and/or β-1,3-glucanase in the apoplastic space of a transgenic plant.

In another embodiment of the present invention, it may be adyantageous to engineer a plant with a gene construct comprising a sequence encoding a plant chitinase and β-1, 3-glucanase protein or polypeptide operably associated with a tissue- or developmental-specific promoter, such as, but not limited to, the CHS promoter, the PATATIN promoter, etc.

In yet another embodiment of the present invention, it may be advantageous to transform a plant with a gene construct comprising a sequence encoding a plant chitinase and β-1,3-glucanase protein or polypeptide operably linked to a modified or artificial promoter. Typically, such promoters, constructed by recombining structural elements of different promoters, have unique expression patterns and/or levels not found in natural promoters. See, e.g., Salina et al., 1992, Plant Cell 4:1485–1493, for examples of artificial promoters constructed from combining cis-regulatory elements with a promoter core.

In yet an additional embodiment of the present invention, the expression of a chitinase and β-1,3-glucanase polynucleotide may be engineered by increasing the copy number of the gene encoding the desired protein or polypeptide-using techniques known in the art.

5.5 Transformation of Plants and Plant Cells

Plants and plant cells may be transformed using any method known in the art. In an embodiment of the present invention, Agrobacterium is employed to introduce the gene construct into plants. Such transformation preferably uses binary Agrobacterium T-DNA vectors (Bevan, 1984, Nuc. Acid Res. 12:8711–8721), and the co-cultivation procedure (Horsch et al., 1985, Science 227:1229–1231). Generally, the Agrobacterium transformation system is used to engineer dicotyledonous plants (Bevan et al., 1982, Ann. Rev. Genet 16:357–384; Rogers et al., 1986, Methods Enzymol. 118:627–641). The Agrobacterium transformation system may also be used to transform, as well as transfer, DNA to monocotyledonous plants and plant cells. (see Hemalsteen et al., 1984, EMBO J 3:3039–3041; Hooykass-Van Slogteren et al., 1984, Nature 311:763–764; Grimsley et al., 1987, Nature 325:1677–179; Boulton et al., 1989, Plant Mol. Biol. 12:31–40.; and Gould et al., 1991, Plant Physiol. 95:426–434).

In other embodiments, various alternative methods for introducing recombinant nucleic acid constructs into plants and plant cells may also be utilized. These other methods are particularly useful where the target is a monocotyledonous plant or plant cell. Alternative gene transfer and transformation methods include, but are not limited to, particle gun bombardment (biolistics), protoplast transformation through calcium-, polyethylene glycol (PEG)- or electroporation-mediated uptake of naked DNA (see Paszkowski et al., 1984, EMBO J 3:2717–2722, Potrykus et al. 1985, Molec. Gen. Genet. 199:169–177; Fromm et al., 1985, Proc. Nat. Acad. Sci. USA 82:5824–5828; and Shimamoto, 1989, Nature 338:274–276) and electroporation of plant tissues (D'Halluin et al., 1992, Plant Cell 4:1495–1505). Additional methods for plant cell transformation include microinjection, silicon carbide mediated DNA uptake (Kaeppler et al., 1990, Plant Cell Reporter 9:415–418), and microprojectile bombardment (see Klein et al., 1988, Proc. Nat. Acad. Sci. USA 85:4305–4309; and Gordon-Kamm et al., 1990, Plant Cell 2:603–618). In any methods, selectable markers may be used, at least initially, in order to determine whether transformation has actually occurred. Useful selectable markers include enzymes which confer resistance to an antibiotic, such as gentamycin, hygromycin, kanamycin and the like. Alternatively, markers which provide a compound identifiable by a color change, such as GUS, or luminescence, such as luciferase, may be used.

The chimeric gene may also comprise a gene switch mechanism which determines under what conditions or when the coding sequence is to be expressed. The gene switch may be a chemically induced promoter or a temperature controlled promoter, for example.

According to the present invention, a wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., Arabidopsis).

5.6 Screening of Transformed Plants and Plant Cells

According to the present invention, desired plants may be obtained by engineering one or more of the gene constructs expressing a chitinase and β-1,3-glucanase as described herein into a variety of plant cell types, including but not limited to, protoplasts, tissue culture cells, tissue and organ explants, pollens, embryos, as well as whole plants. In an embodiment of the present invention, the engineered plant material is selected or screened for transformants (those that have incorporated or integrated the introduced gene construct(s)) following the approaches and methods described below. An isolated transformant may then be regenerated into a plant. Alternatively, the engineered plant material may be regenerated into a plant before subjecting the derived plant to selection or screening for the marker gene traits. Procedures for regenerating plants from plant cells, tissues or organs, either before or after selecting or screening for marker gene(s), are well known to those skilled in the art.

A transformed plant cell, callus, tissue or plant may be identified and isolated by selecting or screening the engineered plant material for traits encoded by the marker genes present on the transforming DNA. For instance, selection may be performed by growing the engineered plant material on media containing inhibitory amount of the antibiotic or herbicide to which the transforming gene construct confers resistance. Further, transformed plants and plant cells may also be identified by screening for the activities of any visible marker genes (e.g., the 3-glucuronidase, luciferase, B or Cl genes) that may be present on the recombinant nucleic acid constructs of the present invention. Such selection and screening methodologies are well known to those skilled in the art.

Physical and biochemical methods may also be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme activity, where such gene products are encoded by the gene construct; 4) protein gel electrophoresis (PAGE), Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

5.7 Transgenic Plants Expressing an Engineered Chitinase and β-1,3-Glucanase Polynucleotides Transgenic plants are generated that express an engineered chitinase and β-1,3-glucanase gene. A transgenic plant expressing a chitinase and β-1,3-glucanase is less susceptible to the pathogenic effects of the pathogen of interest. Transgenic plants may be made using any of the techniques known in the art as described for plant chitinase and β-1,3-glucanase expressing transgenic plants, supra.

Transgenic plants expressing one or more chitinase and β-1,3-glucanase gene polynucleotides capable of rendering said plants more resistant to a pathogen of interest may be from any plant species, plant genus, plant family, plant order, plant class, plant division of the kingdom of plants. See, e.g., U.S. Pat. Nos. 5,889,189; 5,869,720; 5,850,015; 5,824,842; PP10,742; PP10,704; PP10,682, which recite plant species, genuses, families, orders, classes and divisions in which the chitinase and β-1,3-glucanase genes may be used.

Examples of plants are monocots, dicots, crop plants (i.e., any plant species grown for purposes of agriculture, food production for animals including humans, plants that are typically grown in groups of more than about 10 plants in order to harvest for any reason the entire plant or a part of the plant, e.g., a fruit, a flower or a crop, e.g., grain, that the plants bear, etc.), trees (i.e., fruit trees, trees grown for wood production, trees grown for decoration, etc.), flowers of any kind (i.e., plants grown for purposes of decoration, for example, following their harvest), cactuses, etc.

Further examples of plants in which the chitinase and β-1,3-glucanase genes may be expressed include Viridiplantae, Streptophyta, Embryophyta, Tracheophyta, Euphyllophytes, Spermatophyta, Magnoliophyta, Liliopsida, Commelinidae, Poales, Poaceae, Oryza, *Oryza sativa*, Zea, *Zea mays*, Hordeum, *Hordeum vulgare*, Triticum, *Triticum aestivum*, Eudicotyledons, *Core eudicots*, Asteridae, Euasterids, Rosidae, Eurosids II, Brassicales, Brassicaceae, Arabidopsis, Magnoliopsida, Solananae, Solanales, Solanaceae, Solanum, Nicotiana.

Also included are, for example, crops of particular interest including Solanaceae, including processing and fresh market tomatoes, pepper and eggplant; leafy plants, including lettuce and spinach; Brassicas, including broccoli, brussels sprouts, calabrese, kale, cauliflower, red cabbage and white cabbage; cucurbits, including cucumber, melon, watermelon, zucchini and squash; large seeded plants, including peas, beans and sweetcorn; rooted plants, including carrots and onions; vegetatively propagated plants, including berries, grapes, banana, pineapple and rosaceous fruit and nut crops; and tropical crops, including mango and papaya.

Thus, the invention has use over a broad range of plants including, but not limited to, species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Panneserum, Persea, Phaseolus, Pistachia, Pisum, Pyrus, Prunus, Raphanus, Ricinus, Secale, Senecio, Sinapis, Solanum, Sorghum, Theobromus, Trigonella, Titicum, Vicia, Vitis, Vigna, and Zea.

5.8 Polynucleotide Constructs For Expression of Engineered Gene in Transgenic Plants A polynucleotide construct capable of directing the expression of an engineered chitinase and β-1,3-glucanase gene product in a transgenic plant of interest is constructed using general recombinant DNA and cloning techniques known in the art of biotechnology, see, e.g., Sambrook et al., supra; Ausubel et al., supra. Such a polynucleotide construct typically comprises a polynucleotide sequence that encodes an engineered chitinase and β-1,3-glucanase gene product and one or more regulatory polynucleotide sequence. Regulatory sequences useful for the polynucleotide construct of the invention include, but are not limited to, a promoter, an enhancer, an intron, a splice donor, a splice acceptor, a polyadenylation sequence, a RNA stability regulating sequence, or an element of any one of the above (e.g., promoter elements including, but not limited to, a TATA box).

The polynucleotide construct comprises one or more regulatory elements capable of directing the expression of the engineered chitinase and β-1,3-glucanase gene product of the invention. In a preferred aspect, the regulatory elements are capable of directing expression in a plant species in which expression of the engineered chitinase and β-1,3-glucanase gene product is desired. In another preferred aspect, the regulatory elements are capable of directing expression in a cell type in which expression of the engineered chitinase and β-1,3-glucanase gene product is desired in the plant species of interest.

Regulatory elements useful for the polynucleotide construct of the present invention are known to those of skill in the art, for example, promoter and enhancer elements of genes known to be expressed in the cell type and plant species of interest. A promoter useful for expression of the engineered chitinase and β-1,3-glucanase gene product in a cell type of a plant species of interest may also be isolated using routine experimentation, for example, by isolating a promoter region of a gene known to be expressed in the desired fashion. For example, one may screen a genomic library with a cDNA probe specific for the 5' end of a messenger RNA known to be expressed in the cell type of interest of the plant species of interest. Such a 5' end cDNA probe should preferably be only about 100 base pairs to about 300 base pairs so that the clones identified in the genomic library are likely to include the 5' end of the gene possibly including the promoter region of the gene for which the probe is specific. The promoter region typically includes about 1,000 to about 2,000 base pairs upstream of the transcription initiation site. Thus, a promoter useful for the expression of the engineered chitinase and β-1,3-glucanase genes of the present invention is a polynucleotide from about 2,000 base pairs upstream to about 50 base pairs downstream of the transcription initiation site of a gene known to be expressed in the cell type of interest in the plant species of interest, or is a portion of the polynucleotide.

In order to facilitate the proper processing of the engineered chitinase and β-1,3-glucanase gene product, it may be necessary to include a nucleotide stretch that encodes a peptide sequence necessary for such processing. For example, a peptide sequence which is recognized by and functional in the transgenic host plant, for example, to facilitate the entry of the chitinase and β-1,3-glucanase gene product into the endoplasmic reticulum may be necessary, i.e., signal sequence.

5.9 Assays for Testing an Engineered Resistant Plant Line

Plant lines generated using methods of the present invention that express an engineered chitinase and β-1,3-glucanase gene product are more resistant to the pathogenic effects of a pathogen of interest when compared to a plant line of the same species that does not express the engineered chitinase and β-1,3-glucanase gene product (i.e., a wild-type plant). The increased resistance of a plant line generated using methods of the invention may be assayed for by any technique known to the skilled artisan. For example, one may infect a plant of the generated plant line and a plant of a wild-type plant line with a pathogen of interest. After such infection, the plant of the generated plant line will have at least an approximately 20% higher probability of surviving infection than the wild-type plant, more preferably at least about 40%, more preferably at least about 60% and most preferably at least about 80%.

Another way of testing a trangenic plant made using the methods of the invention is by testing for necrosis inducing activity, for example, as described in Mahe et al., 1998, J. Peptide Res. 52:482–494. Thus, one can express an engineered chitinase and β-1,3-glucanase gene in a transgenic plant and infect the transgenic plant with the pathogen of interest. For example, when applying a pathogen to the transgenic plant expressing the engineered chitinase and β-1,3-glucanase gene, one would observe clear necrosis or severe spreading necrosis in the wild-type plant but not in a transgenic plant of the plant line from which the transgenic plant was derived.

Necrotic cell death can also be observed using histochemical staining reactions in addition to visual inspection.

The following examples are provided to further illustrate the current invention but are not provided to in any way limit the scope of the current invention.

6. EXAMPLES

6.1 Materials and Methods

Plant Material

*Brassia juncea* plants were grown in a growth chamber at 22–24° C. under a 12 h light/12 h dark cycle.

Screening a *B. juncea* cDNA Library for Chitinase Clones

A pair of oligonucleotide primers, 5'GGTGGATGGGCTACAGCACCAGAC3'(SEQ ID NO:10) and 5'GCCACGTCCACACTCCAA3' (SEQ ID NO:11), were synthesized for PCR amplification of a 414 bp fragment (nucleotides 1625–2038) of the Arabidopsis chitinase gene (Samac et al., 1990, Plant Physiol 93:907–914). The nucleotide sequence of this fragment which corresponds to a conserved chitinase domain was confirmed before use in screening a *B.juncea* cDNA library (Pua et al., 1992, Plant Mol Biol 19:54–544) by in situ plaque hybridization at 42° C. in a solution containing 30% deionized formamide (Sambrook et al., 1989, Molecular Cloning: A Laboratory Manual, Cold Spring Harbor Laboratory Press, Cold Spring Harbor, N.Y.). Blots were washed in 0.1×SSC, 0.1% SDS at room temperature.

DNA Sequence Analysis

DNA fragments containing the sequences of interest in M13 mp18 (Yanisch-Perron et al., 1985, Gene 33:103–119) were analyzed using the DNA Sequencing Kit with Sequenase Version 2.0 (UBS, Amersham Life Science) and the GCG sequence analysis program (Genetics Computer Group).

Genomic DNA Isolation and Southern Blot Analysis

For Southern blot analysis, 20 µg DNA isolated (Dellaporta et al., 1983, Plant Mol Biol Reptr 1: 19–21) from *B. juncea* was digested with various restriction endonucleases, separated by electrophoresis in 0.8% agarose gel and blotted onto Hybond-N (Amersham) (Sambrook et al., 1989). The blot was hybridized with the $^{32}$P-labelled BjCHI1 cDNA probe in a solution containing 30% deionized formamide, 6×SSC, 5× Denhardt's, 1% SDS and 500 µg/ml denatured, sonicated salmon sperm DNA at 42° C. overnight. The blot was washed in 0.1×SSC, 0.1% SDS at room temperature and 65° C.

Northern Blot Analysis

20 µg of RNA extracted from leaves of seedlings (Nagy et al., 1988, Plant Molecular Biology Manual p. B4: 1–29. Kluwer Academic Publisher, Dordrecht) was denatured at 50° C. in the presence of glyoxal, separated by electrophoresis in 1.5% agarose gel and blotted onto Hybond-N (Amersham) membranes. Blots were incubated with $^{32}$P-labelled BjCHI1 cDNA in 50% formamide, 1× Denhardt's, 6×SSPE, 0.1% SDS, 100 µg/ml denatured, sonicated salmon sperm DNA and 10% dextran sulfate at 42° C. overnight. The blots were washed in 0.1×SSC, 0.1% SDS at 65° C.

Polymerase Chain Reactions

PCR with primers P1 and P2 or P2 and P3 was carried out with the GeneAmp PCR Reagent Kit (Perkin Elmer). FIG. 1A shows the location of the primers: P1 (5'CCTCCGGTGAGCAATGCG3': SEQ ID NO:12) corresponding to nucleotides 56 to 73, P2 (5'TTAGCGGCGGTGATGAAGG3': SEQ ID NO:13) complementary to nucleotides 554 to 536 and P3 (5'TCCTCCAACCCCGCAGTGT3': SEQ ID NO:14) corresponding to nucleotides 207 to 225. *B. juncea* DNA, denatured at 94° C. for 5 mm, was subjected to PCR with primers for 35 cycles of 94° C. for 1 min, 68° C. for 1 mm and 72° C. for 3 mm. The final extension was carried out at 72° C. for 7 mm. The PCR products electrophoresed in 2% agarose gel were blotted onto Hybond-N (Amersham) membrane for hybridization with the $^{32}$P labelled labeled BjCHI1 cDNA. Reverse transcription-polymerase chain reaction (RT-PCR) was performed according to the protocol of Lasserre et al., 1996, Mol Gen Genet 251:81–90, using total RNA extracted from leaves of seedlings using guanidine thiocyanate (Nagy et al., 1988). Primer P4, 5'CCACTC-GAGGTTGTTGC3' (SEQ ID NO:15) (complementary to nucleotides 750 to 734; FIG. 1A), was annealed to 50 µg total RNA. First-strand cDNA was used as template in PCR with primers P2 and P3 (FIG. 1A). All RT-PCR reactions were done in triplicate.

Preparation of Polyclonal Antibodies Against HbGLU and BjCHI1

A synthetic peptide (SDLQSLTNPSNAKS; SEQ ID NO:16) corresponding to amino acids 94–107 of HbGLU (SEQ ID NO:4) (Chye and Cheung, 1995, Plant Mol. Biol. 29:397–402) was purchased from Chiron Technologies (Australia) and was used to raise polyclonal antibodies in rabbit following Sambrook et al., 1989. A synthetic peptide (YKEEIDKSDPHC; SEQ ID NO:8) corresponding to amino acids 23 1–242 of BjCHI1 SEQ ID NO:2) (Zhao and Chye, 1999, supra) was used for immunization of rabbit to raise polyclonal antibodies and these anti-BjCHI1 antibodies were purchased from Chiron Technologies (Australia). Each peptide was coupled to Keyhole Limpet Hemocyanin (KLH) and mixed with Freund's complete adjuvant for raising antibodies. Blood was collected and antibodies against HbGLU were purified using Protein A Sepharose CL-4B (Pharmacia) and CNBr-activated Sepharose 4B (Pharmacia) columns while antibodies against BjCHI1 were purified using a Thiopropyl-Sepharose 6B (Pharmacia) column.

Infection of *B. juncea* with *R. solani*

*B. juncea* seeds were sowed on autoclaved soil and were incubated in a growth chamber at 24° C. with a day-night regime of 12 h light (08:00–20:00) and 12 h dark (20:00–08:00). Two week-old seedlings were carefully transferred to soil inoculated with a week-old culture of *R. solani*. The fungus was grown at room temperature for one week in potato dextrose broth and was added to the soil 3 days before the seedlings were planted. Leaves were harvested daily from seedlings from 0 to 9 days after transfer to infected soil. Total RNA and total protein were extracted from these leaves for northern blot analysis and western blot analysis, respectively.

Plasmid Constructs that Carries Both the Hevea β-1,3-Glucanase and Brassica Chitinase BjCHI1

A 1.2 kb SmaI-HindII fragment of full-length *H. brasiliensis* β-1,3-glucanase cDNA, designated HbGLU (Chye and Cheung, 1995, Plant Mol. Biol. 29: 397–402) was cloned downstream from the CaMV 35S promoter in the SmaI site of binary plasmid vector pBI121 (Clontech) to generate plasmid pHEV43 (FIG. 7) while a 1.3 kb SmaI fragment of full-length cDNA encoding *B. juncea* chitinase, BjCHI1 (Zhao and Chye, supra) was cloned downstream from the CaMV 35S promoter in the SmaI site of pBI121 (Clontech) to generate plasmid pBj17. Subsequently from pHEV43, a 2.04 kb HindIII fragment containing the CaMV 35S promoter and the HbGLU cDNA was blunt-ended with Klenow and ligated to the SnaBI site within the GUS gene of pBj 17, generating two plasmids pBj47 and pBj48 (FIG. 7). The CaMV 35S promoters in pBj47 are inverted while those in pBj48 are in tandem and each of plasmids pBj47 and pBj48 carries both the HbGLU cDNA and the BjCHI1 cDNA on a single plasmid (FIG. 7). Plasmids pBj17, pBj47 and pHEV43 were used in potato transformation.

6.2 Generation of Transgenic Potato Plants Carrying the Hevea β-1,3-Glucanase and Brassica Chitinase BjCHI1 Constructs Plant Transformation Each of plasmids pHEV43, pBj17, pBj47 and pBI121 was mobilized from *E. coli* strain DH5α into *Agrobacterium tumefaciens* strain LBA4404 by tri-parental mating using helper strain HB101 (pRK2013). Transformation of potato plant (*Solanum tuberosum* L.) variety Desiree by *A. tumefaciens* derivatives harboring one of these plasmids was carried out following the protocol of Dietze et al., 1995, In Potrykus I, Sprangenberg G (eds), Gene Transfer to Plants, New York, Cold Spring Harbor Laboratory, p. 24–29. Transformants were selected on Murashige and Skoog media supplemented with kanamycin (100 μg/ml). Potato tissue cultures were maintained in a growth incubator under a 16 h light/8 h dark regime at 20–25° C. Transgenic $R_0$ potato plants were grown in soil in a growth chamber at 24° C. with a day/night regime of 12 h light/12 h dark.

6.3 Testing the Function of Hevea β-1,3-Glucanase and Brassica Chitinase BjCHI1 Products in Stably Transformed Potato Plants Northern Blot Analysis Total RNA was extracted from whole plants following the method described by Nagy et al., 1988, In: S V Gelvin, R A Schilperoort, (eds), Plant Molecular Biology Manual., Kluwer Academic Publishers, Dordrecht, p.B4:1-29). Twenty (20) μg of RNA was denatured at 50° C. for 30 min in the presence of glyoxal., separated by electrophoresis in 1.5% agarose gel and transferred to Hybond-N membrane (Amersham). Blots were prehybridized for 4–6 h and then hybridized with $^{32}$P-labeled BjCHI1 cDNA or HbGLU cDNA, prepared by random-primed labelling, in a solution containing 50% formamide, 1× Denhardt's, 6×SSPE, 0.1% SDS, 100 μg/ml denatured salmon sperm DNA and 10% dextran sulphate at 42° C. overnight. Blots were washed in 0.1×SSC, 0.1% SDS at 65° C.

Southern Blot Analysis

For Southern blot analysis, 20 μg genomic DNA isolated according to Dellaporta et al., 1983, Plant Mol Biol Rep. 1: 19–21, was digested with restriction endonucleases, separated by electrophoresis in 0.7% agarose gel and blotted onto Hybond-N (Amersham) membranes (Sambrook et al., 1989). The membranes were prehybridized in a solution containing 50% deionized formamide, 6×SSC, 5× Denhardt's, 1% SDS, 100 μg/ml denatured salmon sperm DNA at 42° C. for 4–6 h. The $^{32}$P-labeled BjCHI1 cDNA probe or $^{32}$P-labeled HbGLU cDNA probe was added and hybridized overnight. Membranes were washed in 0.1×SSC, 0.1% SDS at 65° C.

Western Blot Analysis

Total plant protein was prepared following the method described by Kush et al., 1990, Proc Natl Acad Sci USA 87: 1787–1790. 20 μg of total protein was separated by SDS-PAGE and transferred onto Hybond-C (Amersham) membrane as described by Sambrook et al., 1989. In western blot analysis, cross-reacting bands were detected using polyclonal antibodies against BjCHI1 or polyclonal antibodies against HbGLU following the procedures described in the Amplified Alkaline Phosphatase Goat Anti-Rabbit Immunoblot Assay Kit (BioRad)

Preparation of Plant Protein Extracts for Enzyme Assays

Plant protein extracts were prepared according to Boller et al., 1983, Planta 157:22–31. Plants were ground to fine powder in liquid nitrogen, transferred to 0.1 M Na-citrate (pH 5.0) buffer containing 1% (v/v) β-mercaptoethanol and vortexed. Following centrifugation (14,000 rpm for 5 min at 4° C.), the supernatant was removed to another tube, incubated at 50° C. for 10 min and cooled on ice for 10 min. The sample was then centrifuged (14,000 rpm for 5 min at 4° C.), and the supernatant was used as the crude protein in assays for chitinase and β-1,3-glucanase activities. Protein concentration was determined according to Bradford (1976, Anal. Biochem, 72:248–254).

β-1,3-Glucanase Assays

Colorimetric assay for β-1,3-glucanase was carried out according to Abeles and Forrence, 1970, Plant Physiol 45:395–400. The reaction mixture of 100 μl (25 μg) plant protein extract and 100 μl of 2% (w/v) laminarin (Sigma) was incubated at 50° C. for 2 h. The reaction was terminated by addition of 600 μl of dinitrosalicyclic reagent and heating for 5 min at 100° C. Following cooling to room temperature, the contents were diluted 1:20 in water and the absorbance was measured at 500 nm.

Chitinase Assays

Colorimetric chitinase assays were carried out according to Wirth and Wolf, 1990, J. Microbiol Meth 12: 197–205. The reaction mixture of 150 μl of substrate carboxymethyl/chitin/Remazol Brilliant Violet (Loewe Biochemica; 2 mg/ml stock solution), 150 μl of 0.2 M Na-Acetate (pH 5.0) and 300 μl (15 μg) plant protein extract was incubated at 37° C. for 0.5 h. The reaction was terminated by addition of 150 μl of 1N HCl, followed by incubation on ice for 5–10 min, before centrifugation (14,000 rpm for 3 min at 4° C.). The supernatant was used to read absorbance at 550 nm. For the blank, 300 μl of 0.1 M Na-citrate, pH 5.0 buffer was used instead of protein sample.

In vitro Fungal Bioassays Using *Tricoderma viride*

*T. viride* Persoon (ATCC 12582) was cultured on a plate of potato dextrose (Difco) agar (PDA). It was used for in vitro hyphal inhibition tests following Schlumbaum et al., 1986, Nature 324:365–367. A plug of growing *T. viride* culture on PDA was transferred to the center of a fresh PDA plate. Following incubation at 25° C. for 24 h during which the hyphae grew outwards from the center, wells were bored on the outer surface of the PDA, equidistant from the plug. Plant protein extract (50 μg) was added to each well and the plate was further incubated in the dark at 25° C. after which growth inhibition of *T. viride* was observed. Photographs were taken at 16 h and 24 h.

In vivo Bioassays Using *R. solani*

It was previously shown in northern blot analysis that BjCHI1 mRNA is induced by wounding or MeJA treatment (Zhao et al., 1999, supra). Subsequently it was also shown that BjCHI1 is also induced by infection with *Aspergillus niger* infection and by caterpillar infestation (Fung et al., 2002, supra). Here, in vivo bioassays were carried out on young potato plants according to Jach et al., 1995, Plant J. 8:97–109. *R. solani* incubated on solid PDA medium at 25° C. for 5–6 days was inoculated into 100 ml of liquid potato dextrose broth (PDB) and incubated with shaking (100 rpm) at room temperature for 1–2 weeks. Subsequently the culture was transferred to a conical flask containing 500 ml of fresh PDB and further incubated for 3–4 days. This culture was then thoroughly mixed with 6 L of sterilized soil (Bio-Mix Super, The Netherlands) in a plant growth tray containing sterilized 8 L sterilized soil. After 10 days the soil was uniformly mixed and potato plants, previously grown for 2 weeks in sterilized soil from tissue culture, were transplanted into the infected soil and further incubated in a growth chamber at 24° C. under a 12 h light/12 h dark regime. Photographs were taken of potato plants 2 weeks following transplantation to infected soil. Plants grown in sterilized soil without fungus was used as controls.

6.4 Results

BjCHI1 Expression is Induced by *R. solani* Infection

To investigate the effect of fungal induction on BjCHI1 expression, *B. juncea* seedlings were grown in soil preinoculated with the soil fungus, *R. solani*. Our results on FIG. 8a demonstrate that expression of the 1.3 kb BjCHI1 mRNA increases a day following growth in infected soil. FIG. 8b shows that a cross-reacting band with an apparent molecular mass of 37 kDa expected of the mature BjCHI1 protein accumulates from day 3 following growth in infected soil. The 42-kDa faint band above this band is likely a precursor protein (FIG. 8b). The BjCHI1 precursor of calculated molecular mass 42,774 kDa, undergoes post-translational cleavage whereby an N-terminal signal peptide and a C-terminal vacuolar targeting peptide are removed (Zhao and Chye, supra). Our results suggest that BjCHI1 mRNA and its corresponding protein accumulate following *R. solani* infection, implicating its role in fungal defense.

Expression of BjCHI1 and HbGLU in Transgenic Potato Plants

Figure 9A:
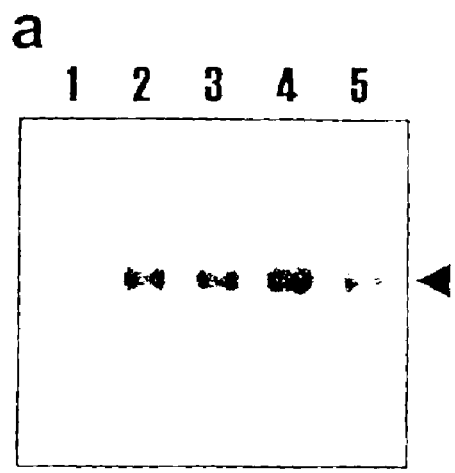
Figure 9B:
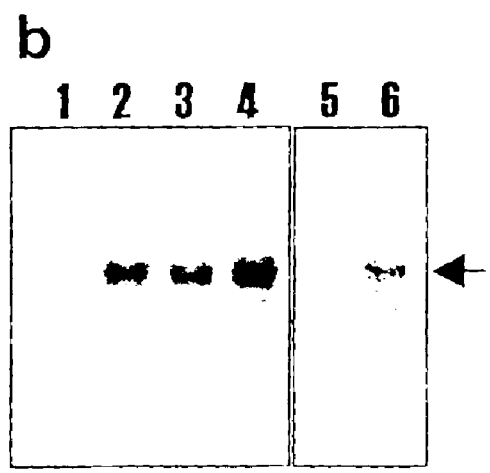

The observation that BjCHI1 expression is induced by *R. solani* infection led us to investigate if its heterologous expression in transgenic potato plant could confer protection against *R. solani*. BjCHI1 cDNA-containing plasmids, pBj17 and pBj47, were each introduced into potato variety Desiree by *A. tumefaciens*-mediated transformation. Plasmid pBj47 also contains the HbGLU cDNA, facilitating us to investigate the effect, if any, of HbGLU in enhancing BjCHI1 action. Plasmid pHEV43 that contains the HbGLU cDNA alone and vector control, pBI121, were also used in potato transformation. About twenty independent kanamycin-resistant putative transgenic plants from each transformation were examined by northern, Southern and western blot analyses. The results of analyses of the representative lines from each transformation that were eventually chosen for experiments of *R. solani* infection, are shown in FIGS. 9, 10 and 11. FIG. 9A shows the presence of a 1.2 kb hybridizing HbGLU mRNA detected using $^{32}$P-labelled HbGLU cDNA in northern blot analysis of transgenic potato lines co-expressing HbGLU and BjCHI1, pBj47-$P_{10}$ (lane 2), pBj47-$P_8$ (lane 3), pBj47-$P_7$ (lane 4) and transgenic potato line expressing HbGLU alone, pHEV-$P_{14}$ (lane 5). This band is absent in untransformed potato (FIG. 9A, lane 1). FIG. 9B shows the expression of the 1.3 kb BjCHI1 hybridizing mRNA as detected with a $^{32}$P-labeled BjCHI1 cDNA probe in transgenic potato lines pBj47-$P_{10}$ (lane 2), pBj47-$P_8$ (lane 3), pBj47-$P_7$ (lane 4) and pBj17-$P_6$ (lane 6). This band is absent in untransformed potato (FIG. 9B, lane 1) and in pBI121 transformed potato (FIG. 9B, lane 5).

Southern Blot Analysis on Transgenic Potato Lines

Subsequently, DNA from these transgenic potato lines was used in Southern blot analysis with $^{32}$P-labeled probes prepared from BjCHI1 or HbGLU cDNA. Results in FIG. 10A show that a 1.2 kb HbGLU EcoRI-hybridizing band is present in transgenic potato lines pHEV43-$P_{14}$ (lane 3), pBj47-$P_7$ (lane 4), pBj47-$P_8$ (lane 5) and pBj47-$P_{10}$ (lane 6) and is absent in both untransformed potato (lane 1) and in pBI121 transformed potato (lane 2). The 1.2 kb EcoRI-hybridizing band corresponds to that shown in the map of pHEV43 (FIG. 7) and contains the full-length HbGLU cDNA. Using a $^{32}$P-labeled BjCHI1 cDNA probe and HindIII-digested DNA in Southern blot analysis (FIG. 10B), a 0.9 kb HindIII-hybridizing band was detected in transgenic potato lines pBj47-$P_7$ (lane 3), pBj47-$P_8$ (lane 4), pBj47-$P_{10}$ (lane 5) and pBj17-$P_6$ (lane 6). This 0.9 kb band corresponds to the fragment between the second and third internal HindIII sites within the BjCHI1 cDNA as shown in the map of pBj17 (FIG. 7). This 0.9 kb hybridizing band was absent in untransformed potato (FIG. 10B, lane 1) and in pBI21 transformed potato (lane 2). When EcoRI-digested DNA was probed with a $^{32}$P-labeled BjCHI1 cDNA probe in Southern blot analysis (FIG. 10C), hybridizing bands of various sizes were seen with transgenic potato lines pBj47-$P_{10}$ (lane 3), pBj47-$P_8$ (lane 4) and pBj47-$P_7$ (lane 5) suggesting that they are independent transgenic lines. Such hybridizing bands were absent in untransformed potato (lane 1) and in pBI121 transformed potato (lane 2).

Protein Detection of BjCHI1 and HbGLU in Transgenic Potato

Figure 11B:
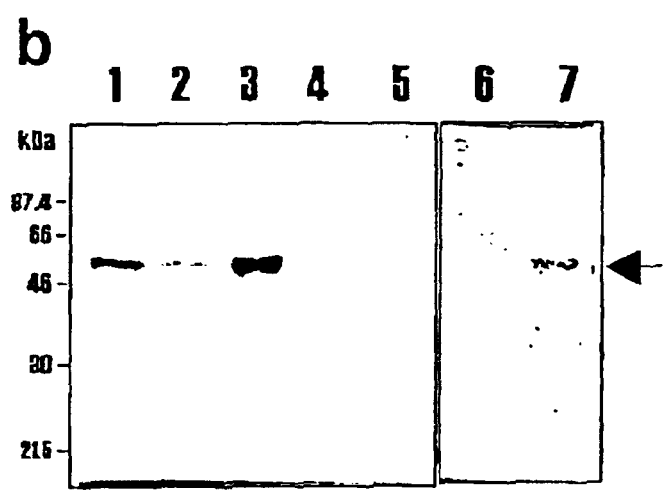

Transgenic plants were further analyzed by western blot analysis using the anti-HbGLU antibodies and anti-BjCHI1 antibodies. Western blot analysis using anti-HbGLU antibodies (FIG. 11A) on crude protein from transgenic potato lines pBj47-$P_7$ (lane 1), pBj47-$P_8$ (lane 2), pBj47-$P_{10}$ (lane 3) and pHEV43-$P_{14}$ (lane 4) show a cross-reacting band with an apparent molecular mass of 35 kDa corresponding to HbGLU. This band was absent in pBI121 transformed potato (FIG. 11A, lane 5) and in untransformed potato (lane 6). Western blot analysis using anti-BjCHI1 antibodies (FIG. 11B) on crude protein from transgenic potato lines pBj47-$P_7$ (lane 1), pBj47-$P_8$ (lane 2), pBj47-$P_{10}$ (lane 3), pHEV43-$P_{14}$ (lane 4), pBI121 transformed potato (lane 5), untransformed potato (lane 6) and transgenic potato line pBj17-$P_6$ (lane 7) shows a cross-reacting BjCHI1 band, with an apparent molecular mass of 52 kDa, in transgenic potato lines pBj47-$P_7$ (lane 1), pBj47-$P_8$ (lane 2), pBj47-$P_{10}$ (lane 3) and pBj17-$P_6$ (lane 7). This band was absent in the transgenic line expressing HbGLU alone, pHEV43-$P_{14}$ (FIG. 11B, lane 4), in pBI121 transformed potato (FIG. 11B, lane 5) and in untransformed potato (FIG. 11B, lane 6). The apparent molecular mass (52 kDa) of potato-expressed BjCHI1 resembles that observed for tobacco-expressed BjCHI1 (Fung et al., 2002, supra), and is larger than that of native BjCHI1 (37 kDa), likely attributed to the inability of proper post-translational processing in heterologous hosts, tobacco and potato.

Chitinase and β-1,3-Glucanase Activity Assay

Figure 12B:
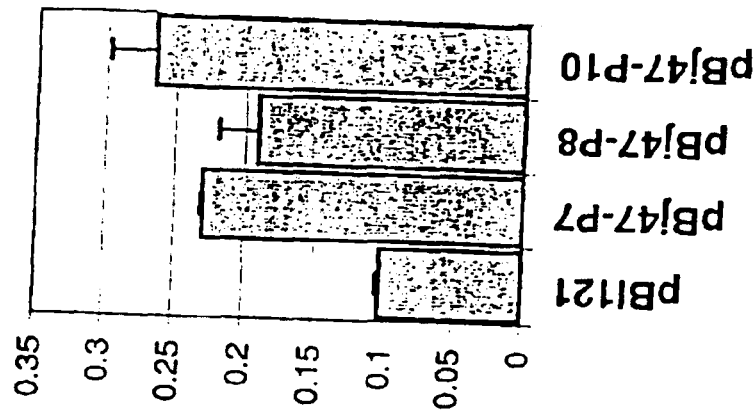
Figure 12A:
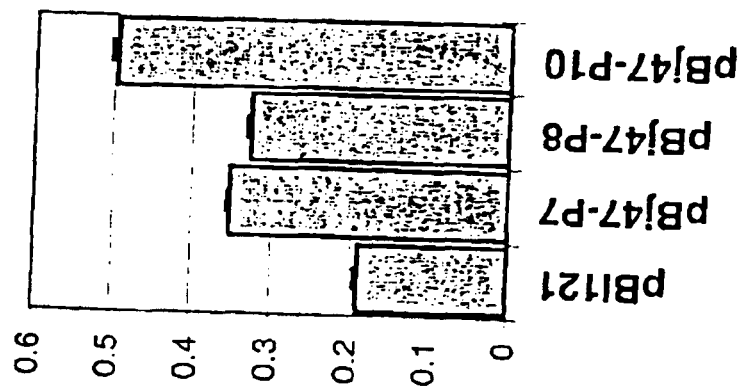

Transgenic potato lines were tested for chitinase and β-1,3-glucanase activity assays and were compared to pBI121 transformed potato (FIG. 12). Glucanase assays (FIG. 12A) using crude protein from pBI121-transformant and transgenic potato lines pBj47-$P_7$, pBj47-$P_8$ and pBj47-$P_{10}$ show that the transgenic lines had higher levels of β-1,3-glucanase activity than that of the pBI121 transformant. Chitinase assays (FIG. 12B) using crude protein show that transgenic potato lines pBj47-$P_7$, pBj47-$P_8$ and pBj47-$P_{10}$ show higher levels of chitinase activities than of the pBI121 transformant. Activities detected in the pBI121 transformant are due to the presence of endogenous potato β-1,3-glucanases and chitinases.

In vitro Bioassay Using *T. viride*

Subsequently crude extracts from transgenic potato lines were tested for in vitro inhibition of *T. viride* growth. Extracts from untransformed potato and a transgenic line transformed with pBI121 were used as controls in these bioassays with buffer as a blank. Photographs taken 16 h (FIG. 13A) and 24 h (FIG. 13B) after addition of protein extracts to wells show that the growth of *T. viride* was inhibited by extract from transgenic potato line pBj47-$P_{10}$ that co-expresses BjCHI1 and HbGLU while inhibition was absent in the buffer-only control (well 2), in extracts from wild-type potato (well 3) and pBI121 transformed potato (well 4). Transgenic potato lines pBj17-$P_6$ expressing BjCHI1 only (well 5) and pHEV43-$P_4$ expressing β-1,3-glucanase only (well 6) show weaker inhibition than that seen with pBj47-$P_{10}$ (well 1).

In vivo Bioassay Using *R. solani*

In vivo bioassays were carried out using young plants grown on soil preinoculated with *R. solani*. Results documented two weeks after transfer to infected soil show that the transgenic potato line pBj47-$P_{10}$ (FIG. 14A) that co-expresses BjCHI1 and HbGLU had slightly better growth than transgenic potato line pBj17-$P_6$ (FIG. 14B) expressing BjCHI1 only. Root development in transgenic potato lines pBj47-$P_{10}$ and pBj17-$P_6$ were much better than that of transgenic potato line pHEV43-$P_{14}$ (FIG. 14C) expressing HbGLU only. Nonetheless root development of transgenic line pHEV43-$P_{14}$ was better than that of untransformed potato (FIG. 14D) suggesting that expression of HbGLU per se conferred some protection. The control plants grown in sterilized soil (not inoculated with *R. solani*) showed root development similar to the pBj47-$P_{10}$ transgenic plants (data not shown). This in vivo bioassay experiment using *R. solani* was repeated with consistent results.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various references are cited herein, the disclosure of which are incorporated by reference in their entirety.

What is claimed is:

1. The recombinant polynucleotide comprising: (a) a first nucleotide sequence of SEQ ID NO:1 or a nucleotide sequence that encodes the amino acid sequence of SEQ ID NO:2; and (b) a second nucleotide sequence of SEQ ID NO:3 or a nucleotide sequence that encodes the amino acid sequence of SEQ ID NO:4.

2. The recombinant polynucleotide of claim 1 further comprising one or more regulatory elements operatively linked to the first nucleotide sequence and the second nucicotide sequence.

3. The recombinant polynucleotide of claim 2, wherein the regulatory element is the 35S promoter of cauliflower mosaic virus.

4. A recombinant cell comprising the recombinant polynucleotide of claim 1.

5. A recombinant cell comprising the recombinant polynucleotide of claim 2.

6. The recombinant cell of claim 4, wherein the cell is a plant cell.

7. The recombinant cell of claim 5, wherein the cell is a plant cell.

8. The recombinant cell of claim 6, wherein the plant cell is from a plant selected from the group consisting of wheat, maize, rice, barley, tomato, apple, pear, strawberry, orange, carrot, potato, sugar beets, yam, lettuce, spinach, petunia, rose, chrysanthemum, pine fir, spruce, sunflower, rape seed, pepper, eggplant, broccoli, brussels sprouts, calabrese, kale, cauliflower, red cabbage, white cabbage, cucumber, melon, watermelon, zucchini, squash, peas, beans,sweetcorn, onion, berries, grapes, banana, pineapple, mango, and papaya.

9. The recombinant cell of claim 7, wherein the plant cell is from a plant selected from the group consisting of wheat, maize, rice, barley, tomato, apple, pear, strawberry, orange, carrot, potato, sugar beets, yam, lettuce, spinach, petunia, rose, chrysanthemum, pine fir, spruce, sunflower, rape seed, pepper, eggplant, broccoli, brussels sprouts, calabrese, kale, cauliflower, red cabbage, white cabbage, cucumber, melon, watermelon, zucchini, squash, peas, beans, sweetcorn, onion, berries, grapes, banana, pineapple, mango, and papaya.

10. The recombinant cell of claim 6, wherein the plant cell is *Solanum tuberosum*.

11. The recombinant cell of claim 7, wherein the plant cell is *Solanum tuberosum*.

12. The recombinant cell of claim 6, wherein the plant cell is from a plant selected from the group consisting of Anacardium, Arabidopsis, Arachis, Asparagus, Asteridae, Atropa, Avena, Brassica, Brassicales, Brassicaceae, Citrus, Citrullus, Capsicum, Carthamus, Cocos, Coffea, Commelinidae, Core eudicots, Cucumis, Cucurbita, Daucus, Elaeis, Embryophyta, Euasterids, Eudicotyledons, Euphyllophytes, Eurosids II, Fragaria, Glycine, Gossypium, Helianthus, Heterocallis, Hordeum, Hordeum vulgare, Hyoscyamus, Lactuca, Liliopsida, Linum, Lolium, Lupinus, Lycopersicon, Magnoliophyta, Magnoliopsida, Malus, Manihot, Majorana, Medicago, Nicotiana, Olea, Oryza, Oryza sativa, Panieum, Panneserum, Persea, Phaseolus, Pistachia, Pisum, Poales, Poaceae, Pyrus, Prunus, Raphanus, Ricinus, Rosidae, Secale, Senecio, Sinapis, Solanaceae, Solanales, Solananae, Solanum, Sorghum, Spermatophyta, Streptophyta, Theobromus, Trigonella, Titicum, Tracheophyta, Triticum, Triticum aestivum, Vicia, Vitis, Vigna, Viridiplantae, Zea, and Zea mays.

13. The recombinant cell of claim 7, wherein the plant cell is from a plant selected from the group consisting of Anacardium, Arabidopsis, Arachis, Asparagus, Asteridae, Atropa, Avena, Brassica, Brassicales, Brassicaceae, Citrus, Citrullus, Capsicum, Carthamus, Cocos, Coffea, Commelinidae, Core eudicots, Cucumis, Cucurbita, Daucus, Elacis, Embryophyta, Euasterids, Eudicotyledons, Euphyllophytes, Eurosids II, Fragaria, Glycine, Gossypium, Helianthus, Heterocallis, Hordeum, Hordeum vulgare, Hyoscyamus, Lactuca, Liliopsida, Linum, Lolium, Lupinus, Lycopersicon, Magnoliophyta, Magnoliopsida, Malus, Manihot, Majorana, Medicago, Nicotiana, Olea, Oryza, Oryza sativa, Panleum, Panneserum, Persea, Phaseolus, Pistachio, Pisum, Poales, Poaceae, Pyrus, Prunus, Raphanus, Ricinus, Rosidae, Secale, Senecio, Sinapis, Solanaceae, Solanales, Solananae, Solanum, Sorghum, Spermatophyta, Strepbophyra, Theobromus, Trigonella, Tilicum, Tracheophyta, Triticum, Triticum aestivum, Vicia, Vitis, Vigna, Viridiplantae, Zea, and Zea mays.

14. A recombinant cell comprising: (a) a first recombinant polynucleotide that comprises the nucleotide sequence of SEQ ID NO: 1 or a nucleotide sequence that encodes the amino acid sequence of SEQ ID NO: 2; and (b) a second recombinant polynucleotide that comprises the nucleotide sequence of SEQ ID NO: 3 or a nucleotide sequence that encodes the amino acid sequence of SEQ ID NO: 4.

15. The recombinant cell of claim 14, wherein the cell is a plant cell.

16. The recombinant cell of claim 15, wherein the plant cell is from a plant selected from the group consisting of wheat, maize, rice, millet, barley, tomato, apple, pear, strawberry, orange, carrot, potato, sugar beets, yam, lettuce, spinach, petunia, rose, chrysanthemum, pine fir, spruce, sunflower, rape seed, pepper, eggplant, broccoli, brussels sprouts, calabrese, kale, cauliflower, red cabbage, white cabbage, cucumber, melon, watermelon, zucchini, squash, peas, beans, sweetcorn, onion, berries, grapes, banana, pineapple, mango, and papaya.

17. The recombinant cell of claim 15, wherein the plant cell is *Solanum tuberosum*.

18. The recombinant cell of claim 15, wherein the plant cell is from a plant selected from the group consisting of Anacardium, Arabidopsis, Arachis, Asparagus, Asteridae, Atropa, Avena, Brassica, Brassicales, Brassicaceae, Citrus, Citrullus, Capsicum, Carthamus, Cocos, Coffea, Commelinidae, Core eudicots, Cucumis, Cucurbita, Daucus, Elaeis, Embiyophyta, Euasterids, Eudicolyledons, Euphyllophytes, Eurosids II, Fragaria, Glycine, Gossypium, Helianthus, Heterocallis, Hordeum, Hordeum vulgare, Hyoscyamus, Lactuca, Liliopsida, Linum, Lolium, Lupinus, Lycopersicon, Magnoliophyta, Magnoliopsida, Malus, Manihot, Malorana, Medicago, Nicotiana, Olea, Oryza, Oryza sativa, Panieum, Panneserum, Persea, Phaseolus, Pistachia, Pisum, Poales, Poaceae, Pyrus, Prunus, Raphanus, Ricinus, Rostdae, Secale, Senecio, Sinapis, Solanaceae, Solanales, Solananae, Solanum, Sorghum, Spermatophyta, Streptophyta, Theobromus, Trigonella, Titicum, Tracheophyta, Triticum, Triticum aestivum, Vicia, Vitis, Vigna, Viridiplantae, Zea, and *Zea mays*.

19. A method for producing a transformed plant which is resistant to fungal pathogens comprising: (a) transforming a plant with the recombinant polynucleotide of claim 1; wherein the recombinant polynucleotide is expressed in said plant.

20. A method for producing a transformed plant which is resistant to fungal pathogens comprising: (a) transforming a plant with a first recombinant polynucleotide comprising the nucleotide sequence of SEQ ID NO: 1 or a nucleotide sequence that encodes the amino acid sequence of SEQ ID NO: 2; (b) transforming said plant with a second recombinant polynucleotide comprising the nucleotide sequence of SEQ ID NO: 3 or a nucleotide sequence that encodes the amino acid sequence of SEQ ID NO: 4; wherein the first and second recombinant polynucleotides are expressed in said plant.

21. The method of claim 19, wherein the fungal pathogen is *Tricoderma viride* or *Rhizoctania solani*.

22. The method of claim 20, wherein the fungal pathogen is *Tricoderma viride* or *Rhizoctania solani*.

23. A transformed potato plant produced by a method comprising: transforming a plant with the recombinant polynucleotide of claim 1.

24. A transformed potato plant produced by a method comprising: (a) transforming a plant with a first recombinant polynucleotide comprising the nucleotide sequence of SEQ ID NO: 1 or a nucleotide sequence that encodes the amino acid sequence of SEQ ID NO: 2; (b) transforming said plant with a second recombinant polynucleotide comprising the nucleotide sequence of SEQ ID NO: 3 or a nucleotide sequence that encodes the amino acid sequence of SEQ ID NO: 4; wherein the first and second recombinant polynucleotides are expressed in said plant.

25. A transformed potato plant comprising a recombinant polynucleotide designated as pBj47 or pBj48.

26. A recombinant polynucleotide designated as or pBj48.

* * * * *